US007799324B2

(12) United States Patent
Bhatia et al.

(10) Patent No.: US 7,799,324 B2
(45) Date of Patent: Sep. 21, 2010

(54) USING UNDIFFERENTIATED EMBRYONIC STEM CELLS TO CONTROL THE IMMUNE SYSTEM

(75) Inventors: Mickie Bhatia, London (CA); Joaquin Madrenas, London (CA); Iris A. Ferber, San Jose, CA (US); Anish Sen Majumdar, Sunnyvale, CA (US)

(73) Assignees: Geron Corporation, Menlo Park, CA (US); University of Western Ontario, London, Ontario (CA)

( * ) Notice: Subject to any disclaimer, the term of this patent is extended or adjusted under 35 U.S.C. 154(b) by 502 days.

(21) Appl. No.: 10/949,702

(22) Filed: Sep. 24, 2004

(65) Prior Publication Data

US 2005/0282272 A1   Dec. 22, 2005

Related U.S. Application Data

(63) Continuation-in-part of application No. 10/862,625, filed on Jun. 7, 2004, which is a continuation of application No. PCT/US02/39091, filed on Dec. 6, 2002.

(60) Provisional application No. 60/338,979, filed on Dec. 7, 2001.

(51) Int. Cl.
*A01N 63/00* (2006.01)
*C12N 5/00* (2006.01)

(52) U.S. Cl. .................... 424/93.21; 435/325
(58) Field of Classification Search ............... 424/93.1; 435/325
See application file for complete search history.

(56) References Cited

U.S. PATENT DOCUMENTS

| | | | |
|---|---|---|---|
| 5,192,553 A | 3/1993 | Boyse et al. |
| 5,409,825 A | 4/1995 | Hoffman et al. |
| 5,437,994 A | 8/1995 | Emerson et al. |
| 5,635,386 A | 6/1997 | Palsson et al. |
| 5,672,346 A | 9/1997 | Srour et al. |
| 5,677,174 A | 10/1997 | Dinsmore |
| 5,750,397 A | 5/1998 | Tsukamoto et al. |
| 5,800,539 A | 9/1998 | Waller |
| 5,807,686 A | 9/1998 | Wagner et al. |
| 5,830,651 A | 11/1998 | Cauley et al. |
| 5,914,268 A | 6/1999 | Keller et al. |
| 6,090,622 A | 7/2000 | Gearhart et al. |
| 6,200,806 B1 | 3/2001 | Thomson |
| 6,280,718 B1 | 8/2001 | Kaufman et al. |
| 2004/0208857 A1* | 10/2004 | Bader et al. ............ 424/93.21 |

FOREIGN PATENT DOCUMENTS

| | | |
|---|---|---|
| EP | 0 455 482 B1 | 8/1997 |
| WO | WO 98/42838 A1 | 10/1998 |
| WO | WO 99/20741 A1 | 4/1999 |
| WO | WO 99/23205 A1 | 5/1999 |
| WO | WO 00/12682 A1 | 3/2000 |
| WO | WO 00/28000 A2 | 5/2000 |
| WO | WO 01/34776 A1 | 5/2001 |
| WO | WO 01/51610 A1 | 7/2001 |
| WO | WO 01/51616 A2 | 7/2001 |
| WO | WO 01/62899 A2 | 8/2001 |
| WO | WO 02/44343 A2 | 6/2002 |
| WO | WO 02/46401 A1 | 6/2002 |
| WO | WO 03/006612 A2 | 1/2003 |

OTHER PUBLICATIONS

Drukker M, Characterization of the expression of MHC proteins in human embryonic stem cell, 2002, PNAS, vol. 99, pp. 9864-9869.*
Heng BC, Transplanted human embryonic stem cells as biological 'catalysts' for tissue repair and regeneration, 2005, Medical Hypotheses, vol. 64, pp. 1085-1088.*
Wu DC, Embryonic stem cell transplantation: potential applicability in cell replacement therapy and regenerative medicine, 2007, Frontiers in Bioscience, vol. 12, pp. 4525-4535.*
2005, Martin et al., Nature Medicine, vol. 11(2), pp. 228-232.*
2008, Grinnemo et al., Cell Tissue Res., vol. 331, pp. 67-78.*
2008, Saric et al., Cells Tissues Organs, vol. 188, pp. 78-90 (Web-Printed Abstract Provided).*
2006, Grinnemo et al., RBM Online, vol. 13(5), pp. 712-714.*
Drukker M, Characterization of the expression of MHC proteins in human embryonic stem cell, 2002, PNAS, vol. 99, pp. 9864-9869.*
Heng BC, Transplanted human embryonic stem cells as biological 'catalysts' for tissue repair and regeneration, 2005, Medical Hypotheses, vol. 64, pp. 1085-1088.*

(Continued)

*Primary Examiner*—Peter Paras, Jr.
*Assistant Examiner*—David Montanari
(74) *Attorney, Agent, or Firm*—E. Stewart Mittler

(57) ABSTRACT

This disclosure provides a system for minimizing the alloreactivity of tissue transplants. The patient is administered with undifferentiated embryonic stem cells or early progenitor cells. This induces a state of inflammatory quiescence or immune unresponsiveness, which in turn enhances engraftment of cells derived from the same stem cell line given for purposes of regenerative medicine.

11 Claims, 8 Drawing Sheets

OTHER PUBLICATIONS

Figure 1:
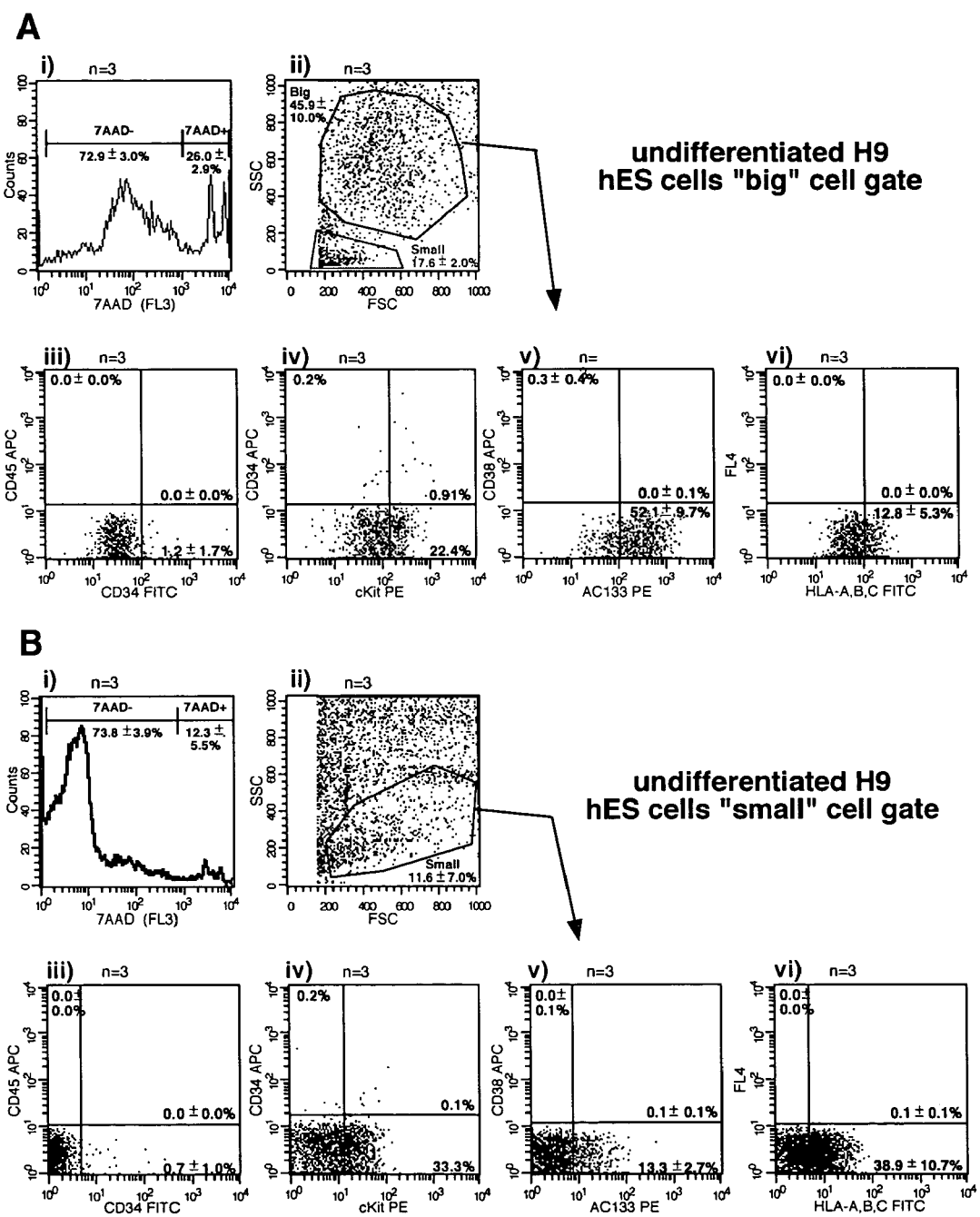

Wu DC, Embryonic stem cell transplantation: potential applicability in cell replacement therapy and regenerative medicine, 2007, Frontiers in Bioscience, vol. 12, pp. 4525-4535.*

Chadwick, K., et al., "Cytokines and BMP-4 promote hematopoietic differentiation of human embryonic stem cells", Blood, (2003) p. 906-915, vol. 102, No. 3.

Li, F., et al., "Bone morphogenetic protein 4 Induces efficient hematopoietic differentiation of rhesus monkey embryonic stem cells in vitro", Blood, (2001) p. 335-342, vol. 98, No. 2.

Lu, S-J., et al., "Hematopoietic Progenitor Cells Derived from Embryonic Stem Cells: Analysis of Gene Expression", Stem Cells, (2002) p. 428-437, vol. 20.

Odorico, J.S., et al., "Multilineage Differentiation from Human Embryonic Stem Cell Lines", Stem Cells, (2001) p. 193-204, vol. 19.

Wang, L., et al., "Endothelial and Hematopoietic Cell Fate of Human Embryonic Stem Cells Originates from Primitive Endothelium with Hemangioblastic Properties", Immunity, (2004) p. 31-41, vol. 21.

"Stem Cells: Scientific Progress and Future Research Directions," Ch. 3, Department of Health and Human Services, http://stemcells.nih.gov/info/scireport/2001report, 12 pages (2001).

Adelman, D. et al., "Multilineage embryonic hematopoiesis requires hypoxic ARNT activity," Genes Dev. 13:2478-83 (1999).

Allan, D. et al., "Number of viable $CD34^+$ cells reinfused predicts engraftment in autologous hematopoietic stem cell transplantation," Bone Marrow Transplant. 29:967-72 (2002).

Anzai, H. et al., "Self-renewal and differentiation of a basic fibroblast growth factor-dependent multipotent hematopoietic cell line derived from embryonic stem cells," Develop. Growth Differ. 41:51-8 (1999).

Bhardwaj, G. et al., "Sonic hedgehog induces the proliferation of primitive human hematopoietic cells via BMP regulation," Nature Immunol. 2(2):172-8 (2001).

Bhatia, M. et al., "A newly discovered class of human hematopoietic cells with SCID-repopulating activity," Nature Med. 4(9):1038-45 (1998).

Bhatia, M. et al., "Bone morphogenetic proteins regulate the developmental program of human hematopoietic stem cells," J. Exp. Med. 189(7):1139-47 (1999).

Bhatia, M. et al., "Purification of primitive human hematopoietic cells capable of repopulating immune-deficient mice," Proc. Natl. Acad. Sci. USA 94:5320-5 (1997).

Bhatia, M. et al., "Quantitative analysis reveals expansion of human hematopoietic repopulating cells after short-term ex vivo culture," J. Exp. Med. 186(4):619-24 (1997).

Bhatia, V. & Porter, D., "Novel approaches to allogeneic stem cell therapy," Expert Opin. Biol. Ther. 1(1):3-15 (2001).

Biesecker, L. & Emerson, S., "Interleukin-6 is a component of human umbilical cord serum and stimulates hematopoiesis in embryonic stem cells in vitro," Exp. Hematol. 21:774-8 (1993).

Bigas, A. et al., "Generation of hematopoietic colony-forming cells from embryonic stem cells: synergy between a soluble factor from NIH-3T3 cells and hematopoietic growth factors," Blood 85(11):3127-33 (1995).

Bock, T., "Assay systems for hematopoietic stem and progenitor cells," Stem Cells 15(Suppl 1):185-95 (1997).

Bonnet, D et al., "Cytokine treatment or accessory cells are required to initiate engraftment of purified primitive human hematopoietic cells transplanted at limiting doses into NOD/SCID mice," Bone Marrow Transpl. 23:203-9 (1999).

Burkert, U. et al., "Early fetal hematopoietic development from in vitro differentiated embryonic stem cells," New Biologist 3(7):698-708 (1991).

Chan, R. & Yoder, M., "The multiple facets of hematopoietic stem cells," Curr. Neurovasc. Res. 1(3):197-206 (2004).

Chiu, C-P. et al., "Differential expression of telomerase activity in hematopoietic progenitors from adult human bone marrow," Stem Cells 14:239-48 (1996).

Dang, S. et al., "Efficiency of embryoid body formation and hematopoietic development from embryonic stem cells in different culture systems," Biotechnol. Bioeng. 78(4):442-53 (2002).

Dick, J. et al., "Assay of human stem cells by repopulation of NOD/SCID Mice," Stem Cells 15(Suppl 1):199-203 (1997).

Fandrich, F. et al., "Preimplantation-stage stem cells induce long-term allogeneic graft acceptance without supplementary host conditioning," Nature Med. 8(2):171-8 (2002).

Firpo, M. et al., "Controlled differentiation of human embryonic stem cells," Dev. Biol. 222(1):234 Abstract No. 69 (2000).

Gaffney, P. et al., "FLT-3 Ligand and Marrow Stroma-Derived Factors Promote $CD3\gamma$, $CD3\delta$, $CD3\zeta$, and RAG-2 Gene Expression in Primary Human $CD34^+LIN^-DR^-$ Marrow Progenitors," Blood 91(5):1662-70 (1998).

Gallacher, L. et al., "Identification of novel circulating human embryonic stem cells," Blood 96:1740-7 (2000).

Gallacher, L. et al., "Isolation and Characterization of Human $CD34^-Lin^-$ and $CD34^+Lin^-$ Hematopoietic Stem Cells Using Cell Surface Markers AC133 and CD7," Blood 95:2813-20 (2000).

Gojo, S. et al., "Gene therapy and transplantation," Transplantation 69:1995-9 (2000).

Gunsilius, E. et al., "Hematopoietic Stem Cells," Biomed. Pharmacother. 55:186-94 (2001).

Gutierrez-Ramos, J. & Palacios, R., "In vitro differentiation of embryonic stem cells into lymphocyte precursors able to generate T and B lymphocytes in Vivo," Proc. Natl. Acad. Sci. USA 89:9171-5 (1992).

Haylock, D. et al., "Ex vivo hematopoietic progenitor cell expansion," ImmunoMethods 5(3):217-25 (1994).

Hess, D. et al., "Functional analysis of human hematopoietic repopulating cells mobilized with granulocyte colony-stimulating factor alone versus granulocyte colony-stimulating factor in combination with stem cell factor," Blood 100(3):869-78 (2002).

Itskovitz-Eldor, J. et al., "Differentiation of human embryonic stem cells into embryoid bodies comprising the three embryonic germ layers," Mol. Med. 6(2):88-95 (2000).

Johansson, B. & Wiles, M., "Evidence for involvement of activin A and bone morphogenetic protein 4 in mammalian mesoderm and hematopoietic development," Molec. Cell Biol. 15(1):141-51 (1995).

Johnson-Saliba, M et al., "Gene therapy: optimising DNA delivery to the nucleus," Curr. Drug Targets 2:371-99 (2001).

Josephson, N. et al., "Transduction of SCID repopulating cells with a human foamy virus vector," Blood 11(1):525a Abstract 2257 (2000).

Karanu, F. et al, "Human homologues of Delta-1 and Delta-4 function as mitogenic regulators of primitive human hematopoietic cells," Blood 97(7):1960-7 (2001).

Karanu, F. et al, "The notch ligand jagged-1 represents a novel growth factor of human hematopoietic stem cells," J. Exp. Med. 192(9):1365-72 (2000).

Kaufman, D. & Thomson, J., "Human ES cells—haematopoiesis and transplantation strategies," J. Anat. 200:243-8 (2002).

Kaufman, D. et al, "Hematopoietic colony-forming cells derived from human embryonic stem cells," Proc. Natl. Acad. Sci. USA 98(19):10716-21 (2001).

Kaufman, D. et al., "Directed differentiation of human embryonic stem cells into hematopoietic colony forming cells," Blood 94(10 Suppl. 1):34a Abstract No. 138 (1999).

Kehat, I. et al., "Long term high-resolution, electrophysiological assessment of human embryonic stem cell derived cardiomyocytes: A novel in vitro model for the human heart," Circulation 102(18 Suppl. II):II-4 Abstract No. 6 (2000).

Keller, G. et al., "Hematopoietic commitment during embryonic stem cell differentiation in culture," Molec. Cell. Biol. 13(1):473-86 (1993).

Keller, G., "Embryonic stem cell differentiation: emergence of a new era in biology and medicine," Genes Dev. 19:1129-55 (2005).

Keller, G., "In vitro differentiation of embryonic stem cells," Curr. Opin. Cell Biol. 7(6):862-9 (1995).

Koller, M. et al., "flt-3 ligand is more potent than c-kit ligand for the synergistic stimulation of ex vivo hematopoietic cell expansion," J. Hematother. 5:449-59 (1996).

Koller, M. et al., "Reduced oxygen tension increases hematopoiesis in long-term culture of human stem and progenitor cells from cord blood and bone marrow," Exp. Hematol. 20:264-70 (1992).

Larochelle, A. et al., "Identification of primitive human hematopoietic cells capable of repopulating NOD/SCID mouse bone marrow: implications for gene therapy," Nat. Med. 2(12):1329-37 (1996).

Leary, A. et al., "Leukemia inhibitory factor differentiation-inhibiting activity/human interleukin for DA cells augments proliferation of human hematopoietic stem cells," *Blood* 75(10):1960-4 (1990).

Lim, J. et al., "Proteosome analysis of conditioned medium from mouse embryonic fibroblast feeder layers which support the growth of human embryonic stem cells," *Proteomics* 2:1187-203 (2002).

Ling, V. et al., "In vitro differentiation of embryonic stem cells: immunophenotypic analysis of cultured embryoid bodies," *J. Cell Physiol.* 171:104-15 (1997).

Murdoch, B. et al., "Circulating hematopoietic stem cells serve as novel targets for in utero gene therapy," *FASEB J.* 10:1628-30 (2001).

Nakano, T. et al., "Generation of lymphohematopoietic cells from embryonic stem cells in culture," *Science* 265:1098-101 (1994).

Nakayama, N. et al., "Natural killer and B-lymphoid potential in $CD34^+$ cells derived from embryonic stem cells differentiated in the presence of vascular endothelial growth factor," *Blood* 91(7):2283-95 (1998).

Nakayama, N. et al., "Vascular endothelial growth factor synergistically enchances bone morphogenetic protein-4-dependent lymphohematopoietic cell generation from embryonic stem cells in vitro," *Blood* 95(7):2275-83 (2000).

Ohtsuka, S. et al., "Molecular and biological properties of pluripotent embryonic stem cells," *Gene Ther.* 15:74-81 (2008).

Palacios, R. et al., "In vitro generation of hematopoietic stem cells from an embryonic stem cell line," *Proc. Natl. Acad. Sci. USA* 92:7530-4 (1995).

Perkins, A., "Enrichment of blood from embryonic stem cells in vitro," *Reprod. Fertil. Dev.* 10:563-72 (1998).

Pfeifer, A. et al., "Gene therapy: promises and problems," *Annu. Rev. Genomics Hum. Genet.* 2:177-211 (2001).

Potocnik, A. et al., "In vitro generation of lymphoid precursors from embryonic stem cells," *EMBO J.* 13(22):5274-83 (1994).

Rathjen, J. et al., "Formation of a primitive ectoderm like cell population, EPL cells, from ES cells in response to biologically derived factors," *J. Cell Sci.* 112:601-12 (1999).

Ross, G. et al., "Gene therapy in the United States: a five-year status report," *Human Gene Ther.* 7:1781-90 (1996).

Rosu-Myles, M. et al., "Characterization of chemokine receptors expressed in primitive blood cells during human hematopoietic ontogeny," *Stem Cells* 18:374-81 (2000).

Rosu-Myles, M. et al., "The human hematopoietic stem cell compartment is heterogeneous for CXCR4 expression," *Proc. Natl. Acad. Sci. USA* 97(26):14626-31 (2000).

Schuldiner, M. et al., "Effects of eight growth factors on the differentiation of cells derived from human embryonic stem cells," *Proc. Natl. Acad. Sci. USA* 97(21):11307-12 (2000).

Shamblott, M. et al., "Derivation of pluripotent stem cells from cultured human primordial germ cells," *Proc. Natl. Acad. Sci. USA* 95:13726-31 (1998).

Shamblott, M. et al., "Human embryonic germ cell derivatives express a broad range of developmentally distinct markers and proliferate extensively in vitro," *Proc. Natl. Acad. Sci. USA* 98:113-8 (2001).

Shoji, Y. et al., "Current status of delivery systems to improve target efficacy of oligonucleotides," *Curr. Pharm. Des.* 10(7):785-96 (2004).

Snodgrass, H. et al., "Embryonic stem cells and in vitro hematopoiesis," *J. Cell. Biochem.* 49:225-30 (1992).

Thomson, J. & Odorico, J., "Human embryonic stem cell and embryonic germ cell lines," *TIBTECH* 18:53-7 (2000).

Thomson, J. et al., "Embryonic stem cell lines derived from human blastocysts," *Science* 282:1145-7 (1998).

Thomson, J. et al., "Isolation of a primate embryonic stem cell line," *Proc. Natl. Acad. Sci. USA* 92:7844-8 (1995).

Uzan, G. et al., "Hematopoietic Differentiation of Embryonic Stem Cells: An in Vitro Model to Study Gene Regulation During Megakaryocytopoiesis," *Stem Cells* 14(Suppl. 1):194-9 (1996).

Varnum-Finney, B. et al., "The notch ligand, Jagged-1, influences the development of primitive hematopoietic precursor cells," *Blood* 91(11):4084-91 (1998).

Vaziri, H. et al., "Evidence for a mitotic clock in human hematopoietic stem cells: loss of telomeric DNA with age," *Proc. Natl. Acad. Sci. USA* 91:9857-60 (1994).

Verfaillie, C. et al., "Stem Cells: Hype and Reality," *Hematology Am. Soc. Hematol. Educ. Program*, pp. 369-391 (2002).

Verma, I. et al., "Gene therapy—promises, problems and prospects," *Nature* 389:239-42 (1997).

Wang, L., "Endothelial and hematopoietic stem cell fate of human embryonic stem cells," *Trends Cardiovasc. Med.* 16:89-94 (2006).

Weiss, M., "Embryonic stem cells and hematopoietic stem cell biology," *Hematol. Oncol. Clin. North Am.* 11(6):1185-98 (1997).

Wiles, M., & Keller, G. "Multiple hematopoietic lineages develop from embryonic stem (ES) cells in culture," *Development* 111:259-67 (1991).

Wright, D. et al., "Physiological migration of hematopoietic stem and progenitor cells," *Science* 294:1933-6 (2001).

Xu, C. et al., "Feeder-free growth of undifferentiated human embryonic stem cells," *Nature Biotech.* 19:971-4 (2001).

Yuen, D et al., "Generation of a primitive erythroid cell line and promotion of its growth by basic fibroblast growth factor," *Blood* 91(9):3202-9 (1998).

Zhan, X. et al., "Functional antigen-presenting leucocytes derived from human embryonic stem cells in vitro," *The Lancet* 364:163-71 (2004).

Nasonkin, I. & Koliatsos, V., "Nonhuman sialic acid Neu5Gc is very low in human embryonic stem cell-derived neural precursors differentiated with B27/N2 and noggin: Implications for transplantation," *Exp. Neurol.* 201:525-9 (2006).

Kehat, I. et al., "Electromechanical integration of cardiomyocytes derived from human embryonic stem cells", *Nature Biotechnol.* 22(10) (2004), pp. 1282-1289.

\* cited by examiner

Prk-/- Recipients

Wild Type Recipients

USING UNDIFFERENTIATED EMBRYONIC STEM CELLS TO CONTROL THE IMMUNE SYSTEM

REFERENCE TO RELATED APPLICATIONS

This application is a continuation-in-part of U.S. Ser. No. 10/862,625, filed on Jun. 7, 2004, which is a continuation of PCT/US02/39091 (131/200), filed on Dec. 6, 2002, designating the U.S., and published on Jun. 19, 2003 as WO 03/050251. This application does not claim priority to any applications filed before Dec. 6, 2002.

Incorporated herein by reference in their entirety are U.S. provisional application 60/338,979 filed Dec. 7, 2001, U.S. Pat. No. 6,458,589, and International Patent Publications WO 99/20741; WO 01/51616; WO 01/81549; WO 01/88104; WO 02/44343; WO 03/020920, and WO 03/050251, with respect to the culturing of primate pluripotent stem cells, and the use of pPS derived cells for inducing immunotolerance.

BACKGROUND

Considerable interest has been generated in the field of regenerative medicine by recent work relating to the isolation and propagation of human stem cells of various kinds. Pluripotent stem cells are a particularly promising type of progenitor cell, because they can differentiate into a variety of different tissue types, and have a powerful capacity for self-renewal.

An important source of pluripotent stem cells is early embryonic tissue. Techniques have been developed recently to isolate and culture human embryonic stem (ES) cells (Thomson et al., Science 282:114, 1998; U.S. Pat. Nos. 6,090,622 & 6,200,806) and human embryonic germ (EG) cells (Shamblott et al., Proc. Natl. Acad. Sci. USA 95:13726, 1998; U.S. Pat. No. 6,090,622). International Patent Publications WO 99/20741 and WO 01/51616 (Geron Corp.) provide methods and materials for growing primate-derived primordial stem cells in feeder-free culture, which considerably facilitates the preparation of these cells and their derivatives for human therapy.

Draper et al. (J. Anat. 200:249, 2002) characterized various surface antigens on human ES cells, both before and after differentiation. They found that HLA Class I antigen, and $\beta_2$ microglobulin (the light chain of Class I) were expressed in undifferentiated ES cells, and could be induced to higher levels by treatment with interferon gamma (IFN-γ). Drukker et al. (Proc. Natl. Acad. Sci. USA 99:9864, 2002) characterized the expression of MHC proteins on human embryonic stem (ES) cells. Low levels of MHC Class I antigen was found. Class I expression was higher when the cells were treated with IFN-γ, but not IFN-α OR IFN-β. After the cells were allowed to differentiate, Class I expression was enhanced after treatment by all three interferon isotypes. MHC Class II proteins and HLA-G were not expressed on undifferentiated ES cells, or after early differentiation.

Paradigms have recently been established to cause pluripotent stem cells to differentiate into relatively homogeneous populations of particular tissue types, suitable for transplantation.

U.S. Pat. No, 6,458,589 (Geron Corp.) describes and claims ES-derived cells containing a high proportion of cells having multiple characteristics of human hepatocytes. PCT publication WO 01/88104 (Geron Corp.) describes neural progenitor cell populations obtained by differentiating human ES cells. Patent Publications WO 02/42445 and GB 2374076 (Geron Corp.) provide cell populations derived from pluripotent stem cells that are purged of the undifferentiated cell phenotype.

Methods to differentiate human pluripotent stem cells into cells of the hematopoietic lineage were reported by Li et al. (Blood 15:98, 2001); U.S. Pat. No. 6,280,718 (Wisconsin); and Kaufman et al. (Proc. Natl. Acad. Sci. USA 98:10716, 2001). Coculturing with murine bone marrow cells or yolk sac endothelial cells was used to generate cells with hematopoietic markers.

US 2003/0153082 A1 (Bhatia, Robarts Institute) describes an alternative direct method for generating hematopoietic cells from human ES cells. The undifferentiated cells are put into suspension culture with a mixture of hematogenic cytokines and a bone morphogenic protein. No other cell type needs to be present. The cell populations that are produced have a high proportion of CD45+ve and CD34 +ve cells, and the capacity to generate a high frequency of primary and secondary colonies in a standard CFU assay.

Depending on tissue type, cells made by differentiating ES cells may express histocompatibility antigens capable of eliciting an allograft rejection response when administered to a human patient. Several strategies are available for preventing rejection. Traditional methods include the use of immunosuppressive drugs currently in vogue for treating recipients of solid organ transplants.

An alternative strategy is to induce tolerance in the prospective recipient, so that they accept tissue having the histocompatibility markers of the intended allograft, without otherwise being immunocompromized. Patent publication US 2002/0086005 A1 (Geron Corp.) provides a system for promoting graft acceptance, using a cell population differentiated from ES cells. The differentiated cells induce a state of specific unresponsiveness in the patient. This makes the patient able to accept another cell type made from the same ES cell line, which then regenerates a cellular function that the patient needs.

The invention described in this disclosure provides a new system for regulating the immune response in the context of regenerative medicine or treatment of autoimmune disease.

SUMMARY

This invention provides a system for treating a patient in need of regenerative medicine to make them more receptive to an allograft transplant. MHC mismatch between the tissue and the patient is overcome by treating the patient with pluripotent stem cells that are still in the undifferentiated state. The patient can then accept a cell transplant differentiated from the pPS cells to regenerate a function of which they are in need.

One embodiment of this invention is a method of rendering a subject more receptive to receiving an allograft. The subject is administered with a first cell population of undifferentiated primate pluripotent stem (pPS) cells or early stage progenitor cells obtained therefrom. Exemplary pPS cells are human embryonic stem (hES) cells, or their equivalents, such as can be obtained from a human blastocyst. The first cell population inhibits inflammation in against a second cell population, renders the subject immunotolerant to a second cell population, inhibits an inflammatory response, improves engraftment of the second cell population, or otherwise prevents rejection of the second cell population. The second cell population is administered for purposes of tissue regeneration, and reconstitutes or supplements the function of a cell or tissue needed by the subject. Non-limiting illustrations include hepatocytes, neurons, oligodendrocytes and other glial cells, cardiomyocytes, osteogenic cells, mesenchymal cells, hematopoietic cells, chondrocytes, hormone-secreting cells such as islet cells, and precursors of any of these cell types. The two cell populations are MHC matched, and are ideally derived from the same pPS cell line.

A related embodiment of this invention is a pharmaceutical composition or product combination suitable for administration to a human subject for the purpose of regenerative medicine. Such product combinations may contain a first cell population of cells that promote engraftment, and a second cell population that constitutes the allograft for regenerating the needed tissue function. The two cell populations may be combined for simultaneous administration, or packaged separately for simultaneous or sequential administration to the same subject. Also embodied are methods for preparing, testing, and using such pharmaceutical compositions or combinations.

The cell population that enhances engraftment has as a principal active ingredient pPS cells with an undifferentiated phenotype. Alternatively or in addition, embryoid body (EB) cells and other early cell types bearing phenotypic or morphologic features of early-stage differentiated cells may be used, if they comprise enough early stage cells retaining the graft promoting properties of the undifferentiated cells. The pPS or EB cells can be inactivated beforehand to inhibit or prevent cell division, for example, by irradiating the cells, treating with an inactivating agent, or treating with a fixative.

This invention also provides a system for treating an inflammatory or immunological condition in a subject. Undifferentiated pPS or EB cell populations may be administered at or around the site of the pathology. The system comprises both the use of undifferentiated pPS or EB cells as already described to generate pharmaceutical compositions for inhibiting the immune response or treating these conditions, and the use of such compositions in the course of therapy. Non-limiting illustrations for treatment according to this aspect of the invention include multiple sclerosis, Type I diabetes, thyroiditis, and rheumatoid arthritis.

These and other embodiments of the invention will be apparent from the description that follows.

DRAWINGS

FIG. 1 shows flow cytometry analysis of undifferentiated human embryonic stem (hES) cells. Cells were gated for viability (7AAD −ve; panel i) and size (ii), and then for expression of hematopoietic cell surface markers (iii-vi) in undifferentiated ES cell populations. None of the cells expressed the human hematopoietic marker CD45, and only 1.2% were CD34 +ve (a marker of primitive human hematopoietic cells).

Figure 2:
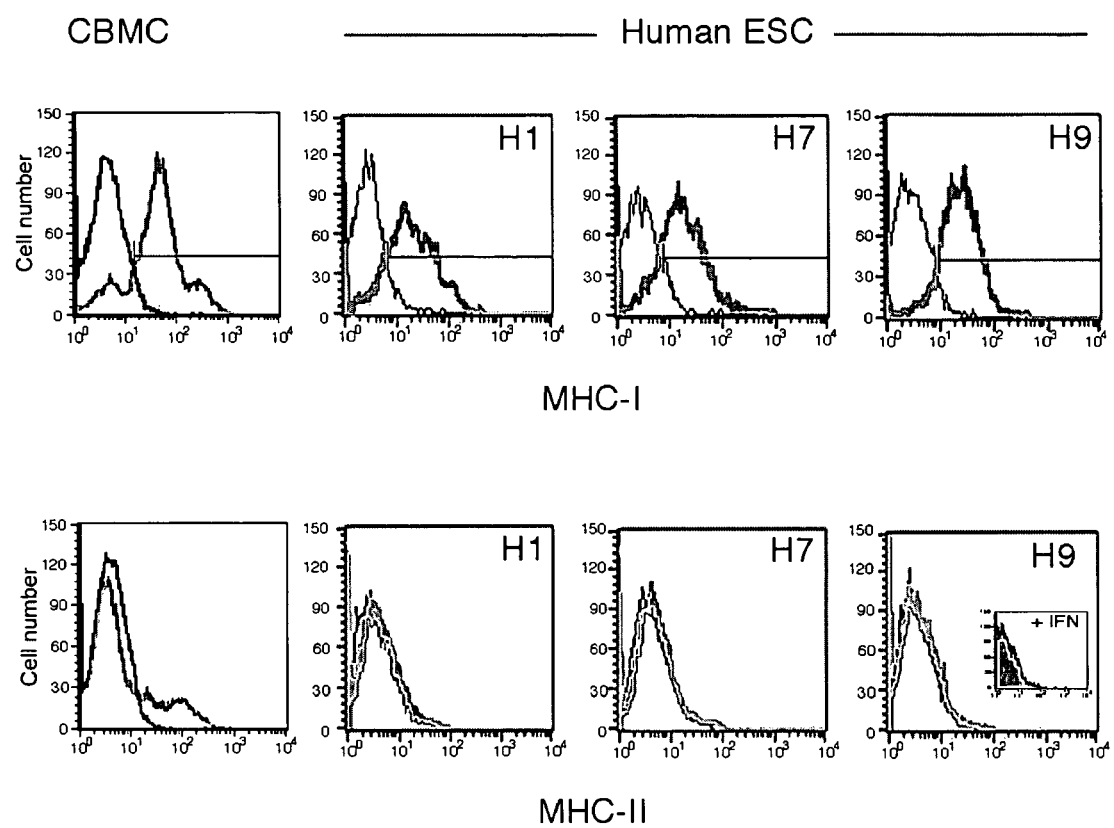

FIG. 2 shows the expression of major histocompatibility complex (MHC) Class I and Class II antigens on cord blood mononuclear cells (CBMC), and undifferentiated hES cell lines H1, H7, and H9. Grey line indicates staining for MHC staining; the solid line indicates antibody control. The undifferentiated hES cells were positive for MHC Class I, but not Class II—even after treatment with interferon gamma (IFN-γ) (inset).

Figure 3:
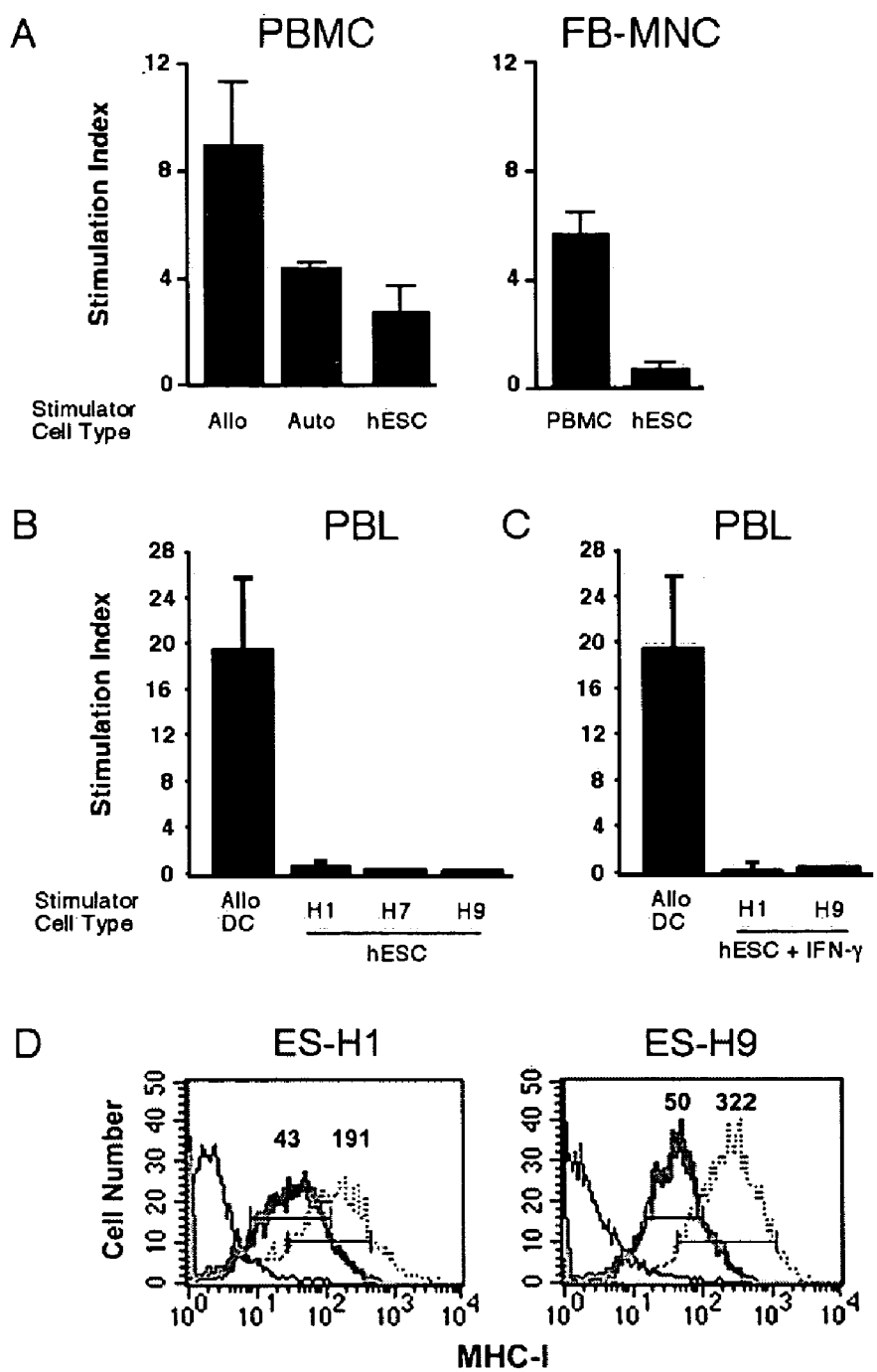

FIG. 3 shows that undifferentiated hES cells are not allostimulatory in a mixed lymphocyte reaction. In Panel A, hES cells failed to stimulate proliferation of allogeneic peripheral blood or cord blood mononuclear cells. In Panel B, all three hES cell lines failed to stimulate proliferation, even after enrichment of the responding population for T cells by monocyte depletion. In another experiment, hES cells were prepared by culturing with IFN-γ to increase MHC Class I expression (Panel D), but still failed to stimulate proliferation of the T cells (Panel C). All of the hES cells used in these experiments had been inactivated by irradiation to prevent proliferation.

Figure 4:
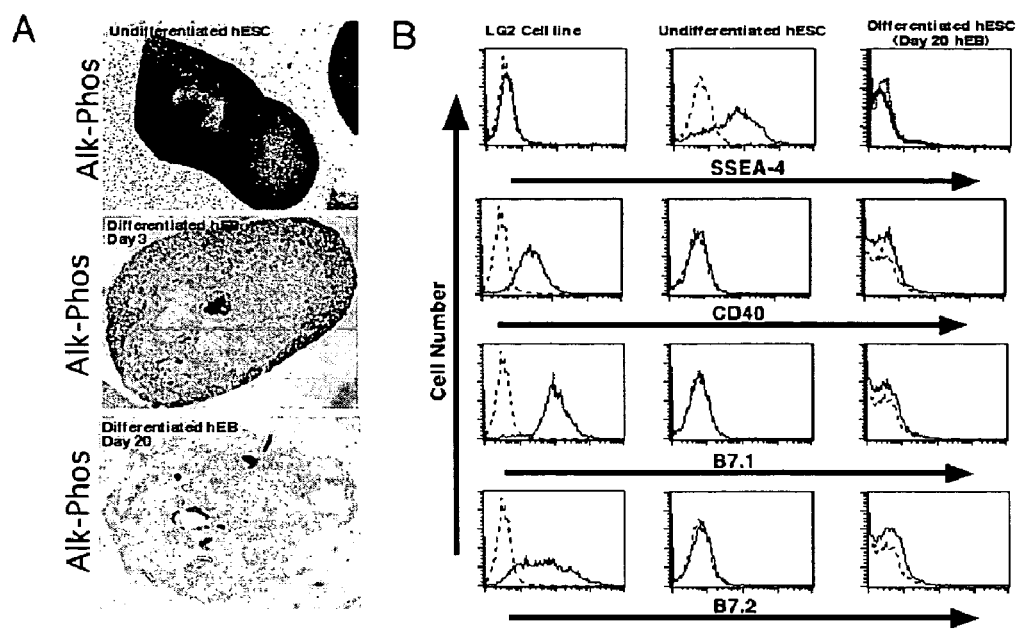
Figure 4:
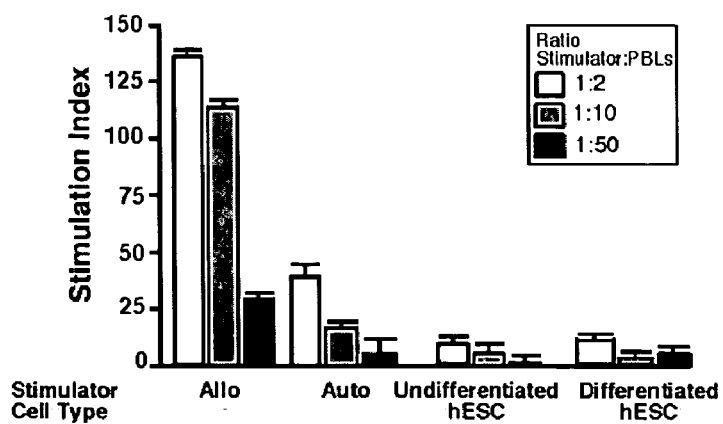

FIG. 4 shows that embryoid body cells (early stage differentiated cells) also lack allostimulatory capacity. As undifferentiated hES cells differentiate to EBs in suspension culture, they lose alkaline phosphatase activity (Panel A) and the undifferentiated cell marker SSEA-4 (Panel B). However, both undifferentiated hES cells and EB cells are even less effective stimulators in a mixed lymphocyte reaction than lymphocytes from allogeneic donors or autologous lymphocytes (Bottom Panel).

Figure 5:
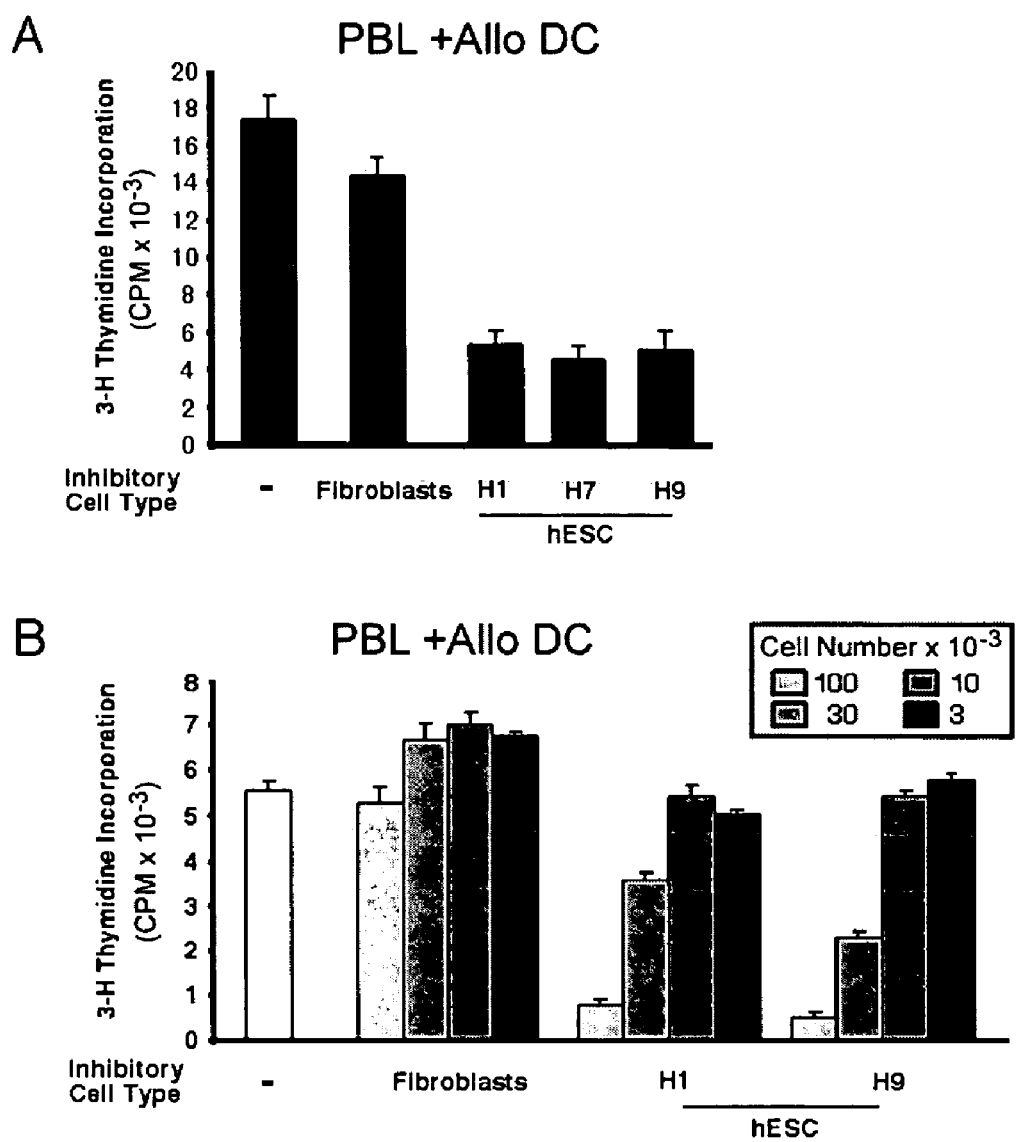

FIG. 5 shows that inactivated hES cells are also able to inhibit a mixed lymphocyte reaction stimulated by third-party antigen-presenting cells. In Panel A, a vigorous proliferative response was observed when T cells were stimulated by allogeneic dendritic cells (DC). Adding human fibroblasts to the culture had minimal effect, but adding undifferentiated hES cells abrogated the response. In Panel B, the inhibitory effect is shown to be dependent on the number of hES cells present in the MLR. The reaction was significantly inhibited by as few as $3 \times 10^4$ hES cells.

Figure 6:
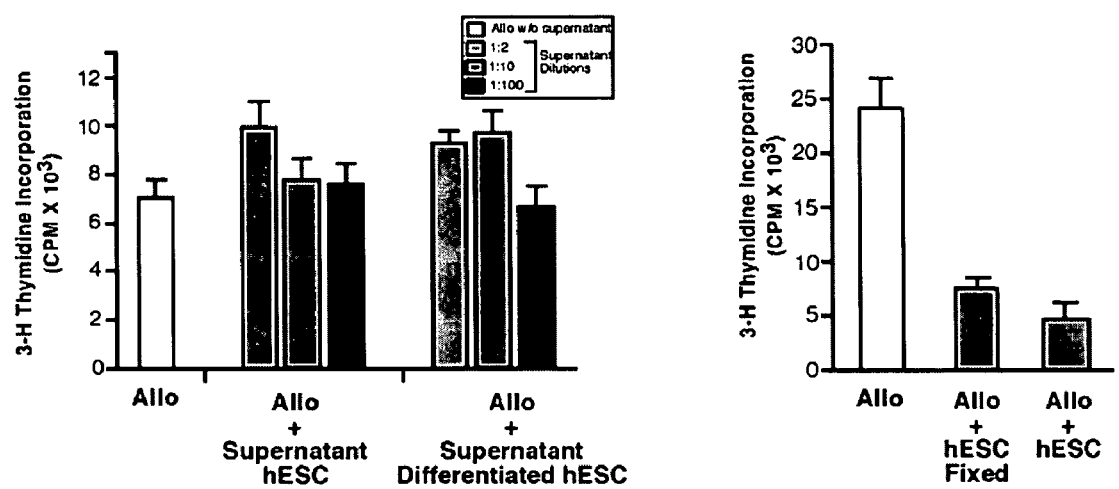

FIG. 6 shows that the immunosuppressive effect of hES cells is due to direct cell contact, not to a secreted factor. Conditioned medium from a culture of undifferentiated hES cells or EBs failed to inhibit thymidine uptake by human peripheral blood lymphocytes stimulated by allogeneic lymphocytes (Left Panel). However, hES cells that had been fixed with paraformaldehyde were just as effective at inhibiting a third-party MLR as unfixed hES cells. The inhibitory properties of hES cells are evidently mediated by a membrane component of the cells.

Figure 7:
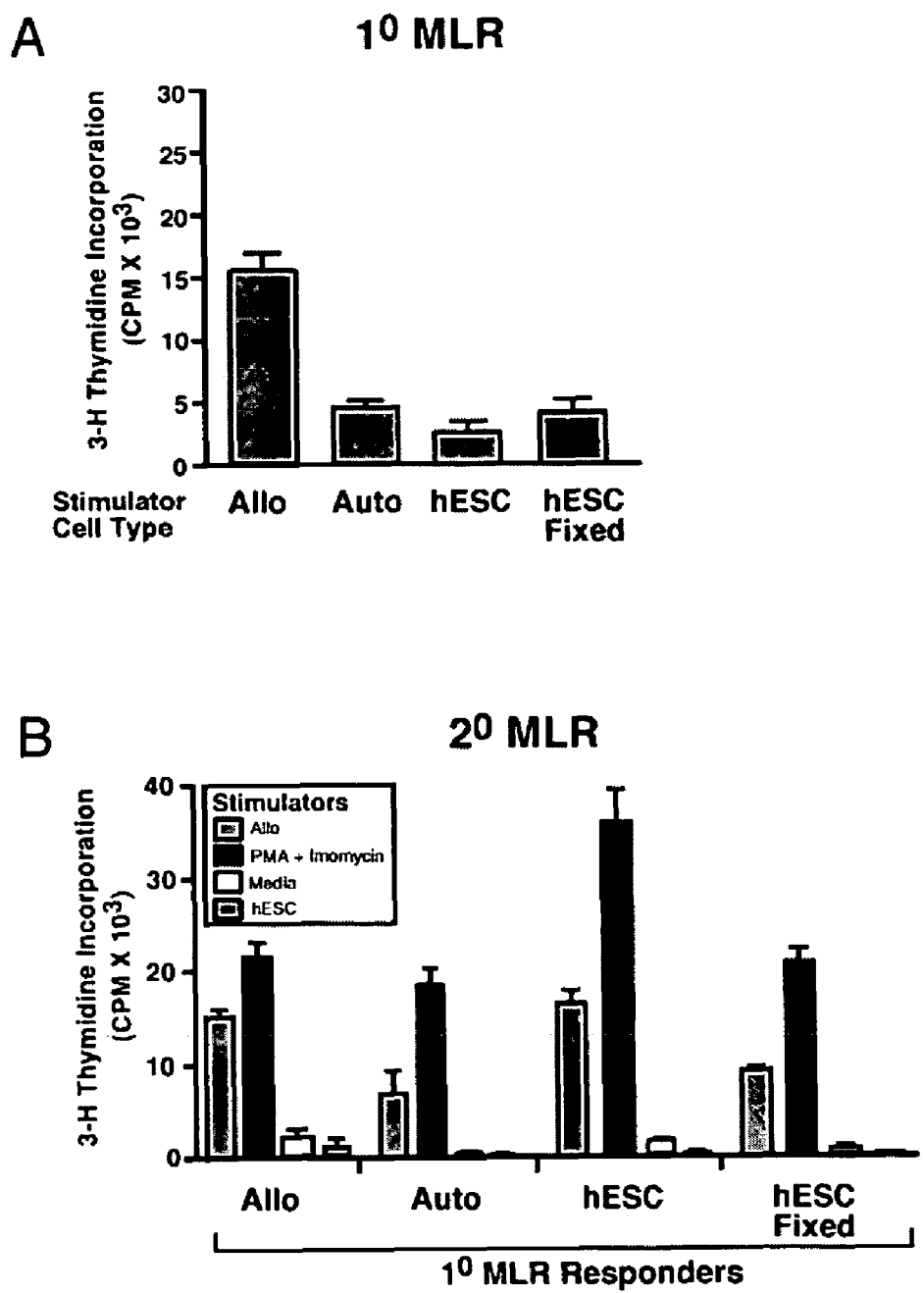

FIG. 7 shows results of an experiment in which the responder cells challenged by various stimulator cells in a primary MLR were rechallenged in a secondary MLR. Regardless of whether the responders had been stimulated or not in the first MLR (Top Panel), they all responded to allogeneic stimulators or PMA plus imomycin in the secondary MLR. This again supports the hypothesis that the most powerful immunoinhibitory effect of the hES cells ensues from direct membrane contact.

Figure 8:
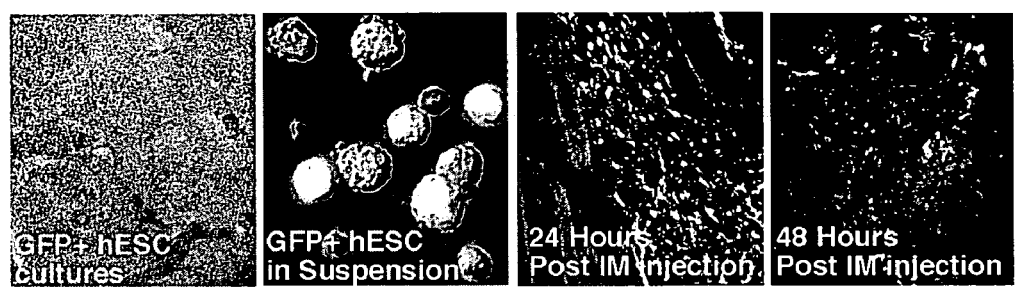
Figure 8:
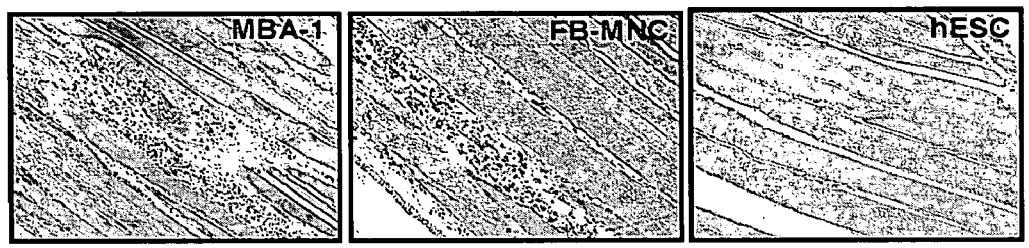
Figure 8:
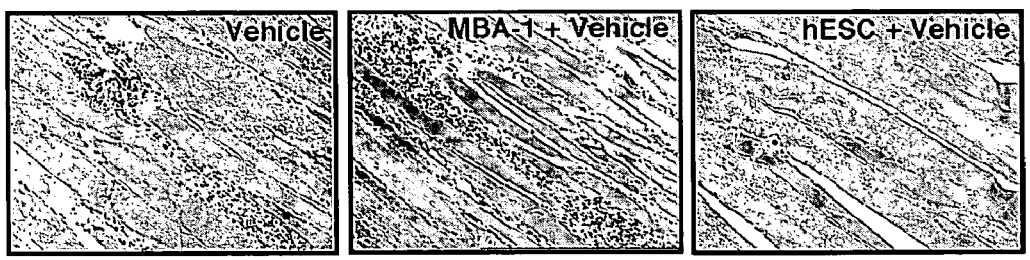

FIG. 8 shows results of experiments in which the antiinflammatory capacity of hES cells was tested in vivo. The Upper Row shows that hES cells expressing green fluorescent protein injected into the quadriceps muscle of recipient mice could be traced in muscle sections taken 24 or 48 hours after administration.

The Middle Row shows the inflammatory response seen in immunodeficient Prk−/− SCID mice, in response to different types of administrated cells. Both MBA-1 megakaryocytes and the fetal mononuclear cells were able to induce a granulocytic infiltration response, but undifferentiated hES cells had no observed effect.

The Lower Row shows the response generated by injection of cells into wild-type CD-1 mice. Injection of endotoxin containing PBS alone induced lymphocyte and granulocyte infiltration at the injection site. However, injection of vehicle together with hES cells completely abrogated leukocyte infiltration (right), whereas MBA-1 cells failed to inhibit infiltration (middle). Undifferentiated hES cells fail to induce a rejection response in this situation. They also apparently prevent host cell infiltration at the injection site, which demonstrates an ability to inhibit inflammation.

DETAILED DESCRIPTION

During a project to characterize the phenotypic and functional features of undifferentiated human embryonic stem (hES) cells, it was unexpectedly discovered that the undifferentiated cells are virtually incapable of stimulating T cell proliferation in a mixed lymphocyte reaction.

In fact, the level of stimulation was found to be lower than stimulation by cells taken from the same donor as the responders (FIG. 3, Panel A). When the responder population was enriched for T lymphocytes by depleting adherent cells, the undifferentiated hES stimulators still failed to activate the responding population (Panel B). When hES cells were treated with interferon gamma, the level of MHC antigen expressed by the cells increased by at least 5-fold (Panel D). Nevertheless, the treated hES cells were still unable to stimulate an alloresponse (Panel C).

The immunosuppressive properties of hES cells are not shared by early-stage cell types from other sources. Mononuclear cells taken from cord blood were quite active as allostimulators in a mixed lymphocyte reaction carried out in the same way (FIG. 3, Panel A, right side). However, embryoid body cells retain the lack of immunogenicity of undifferentiated hES cells.

It was then discovered that hES cells not only fail to cause allostimulation themselves, they also have the ability to prevent stimulation in a three-way MLR containing dendritic cell stimulators and allogeneic T lymphocyte responders (FIG. 5). The inhibitory effect is attributable to direct contact between the undifferentiated hES cell population and the responding T lymphocytes (FIGS. 6 and 7).

Another unexpected finding was obtained when undifferentiated hES cells were injected into experimental animals. MBA megakaryocytes and cord blood mononuclear cells caused a typical host reaction, showed by infiltration of leukocytes to the injection site. In contrast, undifferentiated hES cells induced no infiltration, even in fully immunocompetent mice (FIG. 8).

Following these and other findings, the makers of this invention designed a new system for improving allograft survival in the context of regenerative medicine therapy. According to the invention, hES cells are administered to the subject in order to facilitate later accommodation of cell populations administered for the purpose of tissue regeneration. Because of their inability to stimulate allogeneic T cells, and their ability to inhibit third-party stimulation, hES cells are surprisingly well suited for this purpose. The treated subject becomes refractory to the MHC type of the hES cells, and can be given a population of cells differentiated from the same hES line in order to regenerate a needed tissue function. The special immunological properties of hES cells can also be used to treat other immune and inflammatory conditions by administering them at or near the affected site.

Pluripotent stem cells can be extremely powerful agents to facilitate allograft acceptance. The disclosure that follows provides further information for the use of pPS cells in regenerative medicine and the treatment of autoimmune disease.

DEFINITIONS

Prototype "primate Pluripotent Stem cells" (pPS cells) are pluripotent cells derived from pre-embryonic, embryonic, or fetal tissue at any time after fertilization, and have the characteristic of being capable under appropriate conditions of producing progeny of several different cell types that are derivatives of all of the three germinal layers (endoderm, mesoderm, and ectoderm), according to a standard art-accepted test, such as the ability to form a teratoma in 8-12 week old SCID mice. The term includes both established lines of stem cells of various kinds, and cells obtained from primary tissue that are pluripotent in the manner described.

Included in the definition of pPS cells are embryonic cells of various types, exemplified by human embryonic stem (hES) cells, described by Thomson et al. (Science 282:1145, 1998); embryonic stem cells from other primates, such as Rhesus stem cells (Thomson et al., Proc. Natl. Acad. Sci. USA 92:7844, 1995), marmoset stem cells (Thomson et al., Biol. Reprod. 55:254, 1996) and human embryonic germ (hEG) cells (Shamblott et al., Proc. Natl. Acad. Sci. USA 95:13726, 1998). Other types of pluripotent tent cells are also included in the term. Any cells of primate origin that are capable of producing progeny that are derivatives of all three germinal layers are included, regardless of whether they were derived from embryonic tissue, fetal tissue, or other sources. The pPS cells are preferably not derived from a malignant source. It is desirable (but not always necessary) that the cells be karyotypically normal.

The pPS and hES cells referred to in this description are necessarily a cell population obtained by artificial manipulation: such as the culturing of embryo or blastocyst derived cells in tissue culture in vitro, thereby generating a primary pPS cell population or an established pPS cell line. pPS or hES derived cells are generated by differentiation of cultured pPS cells, not by the natural differentiation of cells within an embryo.

pPS cell cultures are "undifferentiated" when a substantial proportion of stem cells and their derivatives in the population display morphological characteristics of undifferentiated cells, clearly distinguishing them from differentiated cells of embryo or adult origin. It is understood that colonies of undifferentiated cells within the population will often be surrounded by neighboring cells that are differentiated. Undifferentiated pPS cells retain the characteristic of being able to differentiate into progeny representing all three embryonic germ layers. Unless explicitly indicated as undifferentiated, reference to pPS or hES cells may include early stage differentiated cells, such as EB cells.

"Feeder cells" or "feeders" are terms used to describe cells of one type that are co-cultured with cells of another type, to provide an environment in which the cells of the second type can grow. Certain types of pPS cells can be supported by primary mouse embryonic fibroblasts, immortalized mouse embryonic fibroblasts, or human fibroblast-like cells differentiated from hES cell. pPS cell populations are said to be "essentially free" of feeder cells if the cells have been grown through at least one round after splitting in which fresh feeder cells are not added to support growth of the pPS cells.

The term "embryoid bodies" refers to aggregates of early stage differentiated cells that appear when pPS cells overgrow in monolayer cultures, or are maintained in suspension cultures. Embryoid bodies are a mixture of different cell types, typically from several germ layers, distinguishable by morphological criteria and cell markers detectable by immunocytochemistry. "Embryoid body cells" are cells obtained by separating or plating out individual cells or cell clumps from embryoid bodies. The term also refers to functionally analogous populations of pPS derived cells obtained by other methods, such as overgrowth or induced early maturation of pPS cell cultures. EB cell populations comprise cells that have differentiated into early stage progenitors, and retain some immunoresistant and toleragenic effects of undifferentiated hES cells.

A "growth environment" is an environment in which cells of interest will proliferate, differentiate, or mature in vitro. Features of the environment include the medium in which the cells are cultured, any growth factors or differentiation-inducing factors that may be present, and a supporting structure (such as a substrate on a solid surface) if present.

Immune "tolerance" or "unresponsiveness" are general terms that convey only a state of decreased intercellular responsiveness, either in vitro or in vivo. One illustration is a tissue culture reaction where the ability of a stimulator cell (e.g., an allogeneic cell) to induce proliferation or cytokine secretion by a responder cell (e.g., a T lymphocyte) is reduced (e.g., by the presence of third party cells, such as undifferentiated pPS cells). Another illustration is administering an effector cell population (e.g., undifferentiated pPS cells) to a subject, thereby promoting engraftment or inhibiting rejection of a subsequently or simultaneously administered tissue allograft. Inhibiting an inflammatory reaction, generating specific immune tolerance either locally or systemically, or establishing chimerism of some sort, may or may not occur. Immune unresponsiveness may be systemic or only local; transient or part of a memory response; and either allotype-specific or non-specific. The user of this invention need not ascertain such features as long as the cells of this invention are effective in the therapeutic use in which they are employed.

General Techniques

General methods in molecular genetics and genetic engineering are described in the current editions of *Molecular Cloning: A Laboratory Manual*, (Sambrook et al., Cold Spring Harbor); *Gene Transfer Vectors for Mammalian Cells* (Miller & Calos eds.); and *Current Protocols in Molecular Biology* (F. M. Ausubel et al. eds., Wiley & Sons). Cell biology, protein chemistry, and antibody techniques can be found in *Current Protocols in Protein Science* (J. E. Colligan et al. eds., Wiley & Sons); *Current Protocols in Cell Biology* (J. S. Bonifacino et al., Wiley & Sons) and *Current protocols in Immunology* (J. E. Colligan et al. eds., Wiley & Sons.). Reagents, cloning vectors, and kits for genetic manipulation referred to in this disclosure are available from commercial vendors such as BioRad, Stratagene, Invitrogen, ClonTech, and Sigma-Aldrich Co.

Cell culture methods are described generally in the current edition of *Culture of Animal Cells: A Manual of Basic Technique* (R. I. Freshney ed., Wiley & Sons); *General Techniques of Cell Culture* (M. A. Harrison & I. F. Rae, Cambridge Univ. Press), and *Embryonic Stem Cells: Methods and Protocols* (K. Turksen ed., Humana Press). Tissue culture supplies and reagents are available from commercial vendors such as Gibco/BRL, Nalgene-Nunc International, Sigma Chemical Co., and ICN Biomedicals.

Sources of Stem Cells

This invention can be practiced with pluripotent stem cells of various types, particularly stem cells derived from embryonic tissue and have the characteristic of being capable of producing progeny of all of the three germinal layers, as described above.

Exemplary are embryonic stem cells and embryonic germ cells used as existing cell lines or established from primary embryonic tissue of a primate species, including humans. This invention can also be practiced using pluripotent cells obtained from primary embryonic tissue, without first establishing an undifferentiated cell line.

Embryonic Stem Cells

Embryonic stem cells can be isolated from blastocysts of primate species (U.S. Pat. No. 5,843,780; Thomson et al., Proc. Natl. Acad. Sci. USA 92:7844, 1995). Human embryonic stem (hES) cells can be prepared from human blastocyst cells using the techniques described by Thomson et al. (U.S. Pat. No. 6,200,806; Science 282:1145, 1998; Curr. Top. Dev. Biol. 38:133 ff., 1998) and Reubinoff et al, Nature Biotech. 18:399, 2000. Equivalent cell types to hES cells include their pluripotent derivatives, such as primitive ectoderm-like (EPL) cells, outlined in WO 01/51610 (Bresagen).

hES cells can be obtained from human preimplantation embryos (Thomson et al., Science 282:1145, 1998). Alternatively, in vitro fertilized (IVF) embryos can be used, or one-cell human embryos can be expanded to the blastocyst stage (Bongso et al., Hum Reprod 4: 706, 1989). Embryos are cultured to the blastocyst stage, the zona pellucida is removed, and the inner cell masses are isolated (for example, by immunosurgery using rabbit anti-human spleen cell antiserum). The intact inner cell mass is plated on mEF feeder layers, and after 9 to 15 days, inner cell mass derived outgrowths are dissociated into clumps. Growing colonies having undifferentiated morphology are dissociated into clumps, and replated. ES-like morphology is characterized as compact colonies with apparently high nucleus to cytoplasm ratio and prominent nucleoli. Resulting ES cells are then routinely split every 1-2 weeks. Clump sizes of about 50 to 100 cells are optimal.

Propagation of pPS Cells in an Undifferentiated State pPS cells can be propagated continuously in culture, using culture conditions that promote proliferation while inhibiting differentiation. Exemplary serum-containing ES medium is made with 80% DMEM (such as Knock-Out DMEM, Gibco), 20% of either defined fetal bovine serum (FBS, Hyclone) or serum replacement (US 2002/0076747 A1, Life Technologies Inc.), 1% non-essential amino acids, 1 mM L-glutamine, and 0.1 mM β-mercaptoethanol.

Traditionally, ES cells are cultured on a layer of feeder cells, typically fibroblasts derived from embryonic or fetal tissue (Thomson et al., Science 282:1145, 1998). Scientists at Geron have discovered that pPS cells can be maintained in an undifferentiated state even without feeder cells. The environment for feeder-free cultures includes a suitable culture substrate, particularly an extracellular matrix such as Matrigel® or laminin. The pPS cells are plated at >15,000 cells $cm^{-2}$ (optimally 90,000 $cm^{-2}$ to 170,000 $cm^{-2}$). Typically, enzymatic digestion is halted before cells become completely dispersed (say, ~5 min with collagenase IV). Clumps of ~10 to 2,000 cells are then plated directly onto the substrate without further dispersal. Alternatively, the cells can be harvested without enzymes before the plate reaches confluence by incubating ~5 min in a solution of 0.5 mM EDTA in PBS. After washing from the culture vessel, the cells are plated into a new culture without further dispersal. In a further illustration, confluent hES cells cultured in the absence of feeders are removed from the plates by incubating with a solution of 0.05% (wt/vol) trypsin (Gibco) and 0.053 mM EDTA for 5-15 min at 37° C. The remaining cells in the plate are removed and the cells are triturated into a suspension comprising single cells and small clusters, and then plated at densities of 50,000-200,000 cells $cm^{-2}$ to promote survival and limit differentiation.

Feeder-free cultures are supported by a nutrient medium containing factors that promote proliferation of the cells without differentiation (WO 99/20741). Such factors may be introduced into the medium by culturing the medium with cells secreting such factors, such as irradiated (~4,000 rad) primary mouse embryonic fibroblasts, telomerized mouse fibroblasts, or fibroblast-like cells derived from pPS cells (U.S. Pat. No. 6,642,048). Medium can be conditioned by plating the feeders in a serum free medium such as KO DMEM supplemented with 20% serum replacement and 4 ng/mL bFGF. Medium that has been conditioned for 1-2 days is supplemented with further bFGF, and used to support pPS cell culture for 1-2 days (WO 01/51616; Xu et al., Nat. Biotechnol. 19:971, 2001).

Alternatively, fresh or non-conditioned medium can be used, which has been supplemented with added factors (like a fibroblast growth factor or forskolin) that promote proliferation of the cells in an undifferentiated form. Exemplary is a base medium like X-VIVO™ 10 (Biowhittaker) or QBSF™-60 (Quality Biological Inc.), supplemented with bFGF at 40-80 ng/mL, and optionally containing stem cell factor (15 ng/mL), or Flt3 ligand (75 ng/mL). These medium formulations have the advantage of supporting cell growth at 2-3 times the rate in other systems.

Under the microscope, ES cells appear with high nuclear/cytoplasmic ratios, prominent nucleoli, and compact colony formation with poorly discernable cell junctions. Primate ES cells typically express the stage-specific embryonic antigens (SSEA) 3 and 4, and markers detectable using antibodies designated Tra-1-60 and Tra-1-81. Undifferentiated hES cells also typically express the transcription factor Oct-3/4, Cripto, gastrin-releasing peptide (GRP) receptor, podocalyxin-like protein (PODXL), and human telomerase reverse transcriptase (hTERT) (US 2003/0224411 A1), as detected by RT-PCR.

Embryoid Body Cells

Embryoid body cells are early stage differentiated cells obtained by differentiating pPS cells that retain immunoresistant properties of the undifferentiated cells.

Embryoid bodies can be made in suspension culture: undifferentiated pPS cells are harvested by brief collagenase digestion, dissociated into clusters or peeled into strips of cells, and passaged to non-adherent cell culture plates. The aggregates are fed every few days, and then harvested after a suitable period, typically 4-8 days. Other methods for permitting pPS cells to differentiate as cell clumps ore aggregates can also be used: for example, by overgrowth of a donor pPS cell culture, or by plating the cells onto a solid surface low adhesion properties that allows clusters to form and differentiate.

Specific recipes for making EB cells from pPS cells can be found in such authorities as U.S. Pat. No. 6,602,711 (Thomson); WO 01/51616 (Carpenter et al.); US 2003/0175954 A1 (Shamblott & Gearhart); O'Shea, Anat. Rec. (New Anat.) 257:323, 1999; and Chadwick et al., Blood 102:906, 2003.

After a suitable period, such as when the cells have differentiated but some lineage-committed progenitors are still present, the population can be harvested. This may take between 3 or 5 to 10, 20, or 40 days, depending on culture conditions. They can then be separated into individual cells or small clusters of embryoid body cells, using an enzyme like collagenase, and/or a cell dissociation buffer (isotonic formulation of cation chelators and cell-conditioning agents).

Use of pPS Cells in Regenerative Medicine

According to this invention, pPS cells are used to induce immune unresponsiveness. This may be done in preparation for transplantation of an allograft derived from the same pPS cell line that regenerates a cellular function needed by the patient. Immune unresponsiveness decreases the risk of acute or chronic rejection of the allograft. Use of this invention in regenerative medicine involves two cell populations: a first cell type consisting essentially of pPS cells that act to induce the immune unresponsiveness; and a second cell type that regenerates the needed cellular function.

Formulation of pPS Cells as Pharmaceutical Compositions

In accordance with this invention, a population of pPS cells is produced in culture, and then formulated in a medicament suitable for human administration, and effective to induce immune unresponsiveness. pPS cells are either used in the undifferentiated state, or differentiated into early mixed cell populations such as EB cells that retain the effective toleragenic properties. The pPS cells need not be genetically modified in order to have the desired effect, although genetic modifications are permitted where desirable.

In certain circumstances, there is a concern that undifferentiated pPS cells or early progenitors may grow or differentiate in an uncontrolled fashion after administration, giving rise to malignancies or other unwanted hyperplasia. There are several options to manage this concern. One approach is to equip the cells with a suicide gene (such as thymidine kinase) that renders the prodrug ganciclovir toxic to the cell (U.S. Pat. No. 6,576,464). After immune unresponsiveness has been induced, the undifferentiated pPS cells can then be culled from the subject by administering the corresponding prodrug.

Alternatively, the pPS cells are inactivated during the course of formulation of the pharmaceutical composition to an extent that they are no longer capable of proliferation in vivo, but can still perform the activity needed for immunosuppression (Examples 4 to 8). After the inactivated cells have been administered and performed their function, they dissipate harmlessly away.

Treatment with an effective dose of ionizing radiation (say, ~1000 to ~3000 Rads) is an effective means of inactivating the cells. Alternatively, the cells can be treated with an effective dose of mitomycin c, or some other chemotherapeutic, cross-linking, or alkylating agent. As a third option, the cells can be fixed with paraformaldehyde, glutaraldehyde, or other preservative (Example 7). This disclosure also contemplates use of membrane preparations that have been isolated from pPS cells that retain the contact immunoinhibition properties (due to adhesion proteins or other components) of the undifferentiated cells. For pharmaceutical formulation, the membranes can be fixed and/or reconstituted as vesicles or particles that display the appropriate signaling molecules to effect immune unresponsiveness.

Differentiated Cell Types for Regenerating Tissue Function

A variety of clinically useful cell types can be derived from pPS cells for purposes of regenerative medicine, according to established differentiation protocols.

By way of illustration, neural cells can be generated from pPS cells according to the method described in International Patent Publication WO 01/88104 and WO 03/000868 (Geron Corporation). Undifferentiated pPS cells or embryoid body cells are cultured in a medium containing one or more neurotrophins and one or more mitogens, generating a cell population in which at least ~60% of the cells express A2B5, polysialylated NCAM, or Nestin and which is capable of at least 20 doublings in culture. Exemplary mitogens are EGF, basic FGF, PDGF, and IGF-1. Exemplary neurotrophins are NT-3 and BDNF. The proliferating cells can then be caused to undergo terminal differentiation by culturing with neurotrophins in the absence of mitogen. Cell populations can be generated that contain a high proportion of cells staining for tyrosine hydroxylase, a characteristic of dopaminergic neurons.

Oligodendrocytes can be generated from pPS cells by culturing them as cell aggregates, suspended in a medium containing a mitogen such as FGF, and oligodendrocyte differentiation factors such as triiodothyronine, selenium, and retinoic acid. The cells are then plated onto a solid surface, the retinoic acid is withdrawn, and the population is expanded. Terminal differentiation can be effected by plating on poly-L-lysine, and removing all growth factors. Populations can be obtained in which over 80% of the cells are positive for oligodendrocyte markers NG2 proteoglycan, A2B5, and PDGFRα, and negative for the neuronal marker NeuN. See PCT publication WO 04/007696 (Keirstead).

Hepatocytes can be generated from pPS cells according to the method described in U.S. Pat. No. 6,458,589 and PCT publication WO 01/81549 (Geron Corporation). Undifferentiated pPS cells are cultured in the presence of an inhibitor of histone deacetylase. In an exemplary method, differentiation is initiated with 1% DMSO (4 days), then 2.5 mM of the histone deacetylase inhibitor n-butyrate. The cells obtained can be matured by culturing 4 days in a hepatocyte culture medium containing n-butyrate, DMSO, plus growth factors such as EGF, hepatocyte growth factor, and TGF-α.

Cardiomyocytes or cardiomyocyte precursors can be generated from pPS cells according to the method provided in WO 03/006950. The cells are cultured in a growth environment comprising fetal calf serum or serum replacement, and optionally a cardiotrophic factor that affects DNA-methylation, such as 5-azacytidine. Spontaneously contracting cells can then be separated from other cells in the population, by density centrifugation. Further process steps can include culturing the cells so as to form cardiac bodies, removing single cells, and then dispersing and reforming the cardiac bodies in successive iterations.

Hematopoietic cells can be made by coculturing pPS cells with murine bone marrow cells or yolk sac endothelial cells was used to generate cells with hematopoietic markers (U.S. Pat. No. 6,280,718). Hematopoietic cells can also be made by culturing pPS cells with hematogenic cytokines and a bone morphogenic protein, as described in US 2003/0153082 A1 and WO 03/050251.

Osteoblasts and their progenitors can be generated from pPS cells according to the method described in WO 03/004605. pPS-derived mesenchymal cells are differentiated in a medium containing an osteogenic factor, such as bone morphogenic protein (particularly BMP-4), a ligand for a human TGF-β receptor, or a ligand for a human vitamin D receptor. Cells that secrete insulin or other pancreatic hormones can be generated by culturing pPS cells or their derivatives in factors such as activin A, nicotinamide, and other factors listed in WO 03/050249. Chondrocytes or their progenitors can be generated by culturing pPS cells in microaggregates with effective combinations of differentiation factors listed in WO 03/050250.

In principle, any pPS-derived tissue at risk for allograft rejection will benefit from the graft promoting strategy described in this application.

Use of Cell Combinations in Regenerative Medicine

According to this invention, a subject can be rendered immunoresistant using undifferentiated pPS cells or embryoid body cells, and then given therapy with another pPS derived cell type in order to reconstitute a cellular function of which they are in need. International Patent Publication WO 02/44343 (Geron Corp.) provides several rodent and non-human primate models for evaluating the viability of immune modulating protocols, and subsequent tissue regeneration.

Treatment of human subjects proceeds by administering the undifferentiated cells in such a way to induce immune unresponsiveness to the second cell population. As an aid to quelling local inflammation, the tolerizing cells can be administered to the same site that will receive the regenerating allograft. Alternatively, to effect generalized immunotolerance, the pPS cells can be administered systemically. Immune unresponsiveness can be determined by testing the patient's blood lymphocytes in a one-way mixed lymphocyte reaction, using cells of the allograft as stimulators (Example 4). Successful tolerance induction will be demonstrated by reduction in the proliferative response. Chimerism of the recipient can be evaluated by assessing circulating leukocytes for HLA type, and comparing the results with the HLA type of the patient and the administered pPS cells. Anti-inflammatory effect can be determined by histological examination of the injection site (Example 8). Promoting allograft acceptance or decreasing the rejection response can be determined in a transplant model in which skin allografts are monitored for persistence of the graft cells at the transplant site.

The patient is simultaneously or subsequently administered with compatible neurons, oligodendrocytes, hepatocytes, cardiomyocytes, mesenchymal cells, osteoblasts, hormone-secreting cells, chondrocytes, hematopoietic cells, or some other cell type to treat their condition. After the procedure, they are given the requisite amount of supportive care and monitored by appropriate biochemical markers and clinical criteria for improved function.

Use of pPS Cells for Treating Other Immunological and Inflammatory Conditions

The toleragenic and anti-inflammatory properties of the pPS and EB cells of this invention can also be used for treating immunological and inflammatory disease Conditions that may be amenable to this type of therapy include a wide variety of diseases believed to have an autoimmune etiology: for example, rheumatoid and other forms of arthritis, thyroiditis, Graves' disease, Type I and other forms of diabetes, certain forms of heart disease, Crohn's disease, and multiple sclerosis. The undifferentiated or progenitor cells are prepared according to the principles outlined in the previous section. Compositions are tested and optimized first in a suitable animal model, such as the collagen-induced arthritis (CIA) model for rheumatoid arthritis, the BB rat for Type I diabetes, or the induced experimental autoimmune encephalitis (EAE) model for multiple sclerosis. Validated cell populations and modes of use can then be adapted for human therapy.

Because the effects of these cells is thought to ensue in large part from direct cell contact (Example 7), the therapeutic compositions can be formulated for administration directly in or around the site of the pathology to suppress lymphocyte proliferation in situ: For example, the cells can be administered into the thyroid gland to treat thyroiditis, or at or around an inflamed joint to treat arthritis. Use of the therapeutic cell populations of this invention is ultimately the responsibility of the managing clinician.

Commercial Distribution

The therapeutic population of undifferentiated pPS cells or their equivalent is typically supplied in the form of a pharmaceutical composition, comprising an isotonic excipient prepared under sufficiently sterile conditions for human administration. They can be distributed separately, or in combination with a population of differentiated cells for the purpose of tissue regeneration or repair. Effective cell combinations for use in regenerative medicine can be packaged and distributed in separate containers in kit form, or (for simultaneous administration to the same site) they can be mixed together.

For general principles in formulating cell compositions, the reader is referred to *Cell Therapy: Stem Cell Transplantation, Gene Therapy, and Cellular Immunotherapy*, by G. Morstyn & W. Sheridan eds., Cambridge University Press, 1996. Compositions and combinations intended for pharmacological distribution and use are optionally packaged with written instructions for a desired purpose, such as the reconstitution of hematopoietic function, genetic therapy, induction of immune tolerance or unresponsiveness, or the treatment of particular forms of inflammatory or immune mediated disease.

The following examples are provided as further non-limiting illustrations of particular embodiments of the invention.

EXAMPLES

Example 1

Feeder-Free Propagation of Embryonic Stem Cells

Established lines of undifferentiated human embryonic stem (hES) cells were maintained in a culture environment essentially free of feeder cells.

Conditioned medium prepared in advance using primary mouse embryonic fibroblasts (mEF) isolated according to standard procedures (WO 01/51616). Fibroblasts were harvested from T150 flasks by washing once with $Ca^{++}/Mg^{++}$ free PBS and incubating in 1.5-2 mL trypsin/EDTA (Gibco) for ~5 min. After the fibroblasts detached from the flask, they were collected in mEF medium (DMEM+10% FBS). The cells were irradiated at 4000 rad, counted, and seeded at ~55,000 cells $cm^{-2}$ in mEF medium. After at least 4 h, the medium were exchanged with SR containing ES medium (80% knockout DMEM (Gibco BRL, Rockville Md.), 20% knockout serum replacement (Gibco), 1% non-essential amino acids (Gibco), 1 mM L-glutamine (Gibco), 0.1 mM β-mercaptoethanol (Sigma, St. Louis, Mo.), supplemented with 4 ng/mL recombinant human basic fibroblast growth factor (bFGF; Gibco). About 0.3-0.4 mL of medium was conditioned per $cm^2$ of plate surface area. Before addition to the hES cultures, the conditioned medium was supplemented with another 4 ng/mL of human bFGF.

Plates for culturing the hES cells were coated with Matrigel® (Becton-Dickinson, Bedford Mass.) by diluting stock solution ~1:30 in cold KO DMEM, dispensing at 0.75-1.0 mL per 9.6 $cm^2$ well, and incubating for 4 h at room temp or overnight at 4° C.

hES cell cultures were passaged by incubation in ~200 U/mL collagenase IV for ~5-10 min at 37° C. Cells were harvested by removing individual colonies up with a Pipetman™ under a microscope or scraping, followed by gentle dissociation into small clusters in conditioned medium, and then seeded onto Matrigel® coated plates. About one week after seeding, the cultures became confluent and could be passaged. Cultures maintained under these conditions for over 180 days continued to display ES-like morphology. SSEA-4, Tra-1-60, Tra-1-81, and alkaline phosphatase were expressed by the hES colonies, as assessed by immunocytochemistry, but not by the differentiated cells in between the colonies.

Expression of the undifferentiated hES cell markers was assayed by reverse-transcriptase PCR amplification. The transcription factor Oct-4 is normally expressed in the undifferentiated hES cells and is down regulated upon differentiation. Cells maintained on Matrigel® in conditioned medium for 21 days expressed hTERT and Oct-4. Telomerase activity was measured by TRAP assay (Kim et al., Science 266:2011, 1997; Weinrich et al., Nature Genetics 17:498, 1997). Cells maintained in the feeder-free culture were telomerase positive.

Pluripotency of undifferentiated cells cultured without feeders was determined by differentiating the cells through the formation of embryoid bodies. Confluent monolayer cultures of hES cells were harvested by incubating in 1 mg/mL collagenase for 5-20 min, and dissociated into clusters. They were then plated in non-adherent cell culture plates (Costar) in a medium composed of 80% KO DMEM (Gibco) and 20% non-heat-inactivated FBS (Hyclone), supplemented with 1% non-essential amino acids, 1 mM glutamine, 0.1 mM β-mercaptoethanol. The embryoid bodies were fed every other day by the addition of 2 mL of medium per well. After 4-8 days in suspension, they were then cultured on poly-ornithine coated plates for about 7 days.

Immunocytochemistry showed staining patterns consistent with cells of the neuron and cardiomyocyte lineages, and cells staining for α-fetoprotein, a marker of endoderm lineage. The undifferentiated cells were also tested for their ability to form teratomas by intramuscular injection into SCID mice. Resulting tumors were excised after 78-84 days. Cell types from all three germ layers were identified by histological analysis.

Example 2

Lack of Hematopoietic Phenotype in Undifferentiated hES Cell Cultures

Undifferentiated cells of the H1 hES cell line were analyzed by flow cytometry and colony forming (CFU) assay to determine whether any of the characteristics of hematopoietic cells are present in the undifferentiated state.

Cells were harvested from feeder-free culture by dispersing in Collagenase IV solution (1 mg/mL in KO DMEM); trypsin-EDTA (1% trypsin, 2% EDTA; Gibco); or cell dissociation buffer (CDB) (EDTA and high salt, Gibco). The harvested cells were spun down, resuspended in IMDM (Iscove modified Dulbecco's medium) containing 10% FCS, and then filtered through an 85 μm nylon mesh. They were resuspended in 200 μL PBS containing 3% FCS, and incubated with 2 μL of antibody for 15 min at room temp. The cells were washed twice, and then stained with 15 μL/ml 7AAD (Immunotech) for 15 min at room temp.

FIG. 1 shows the results. The viable cells (gated 7AAD −ve; panel i) were further gated by size (ii) to analyze expression of hematopoietic cell surface markers (iii-vi) in undifferentiated ES cell populations. Events with forward scatter properties below 150 were excluded based on a medium control. Cell percentages are expressed as the mean±SEM, based on the number of independent experiments (n) indicated at the top of each plot.

Undifferentiated H1 (A, B) and H9 cells (C, D) were analyzed for the expression of various human hematopoietic markers (iii-vi), using quadrants based on the respective isotype controls (inset). None of the cells expressed the human hematopoietic marker CD45, and only 1.2% were CD34 +ve (a marker of primitive human hematopoietic cells; panel iii). The cells were analyzed for expression of other primitive hematopoietic markers, including c-Kit (iv), CD38 (v), and AC133 (v). There was virtually no CD38, but 22-33% were c-Kit+ve, and 13 to 52% were AC133 +ve. 12-38% expressed MHC Class I antigen (HLA-A, B, and C) (vi).

CFU assays were conducted as follows. Undifferentiated hES cells were harvested, and $2 \times 10^5$ Trypan Blue negative cells were plated into Methocult™ H4230 methylcellulose (StemCell Technologies Inc., Vancouver BC) containing 50 ng/mL SCF, 10 ng/mL GM-CSF (Novartis), 10 ng/mL IL-3 (Novartis), and 3 U/mL EPO (Amgen). Addition of 25 ng/mL BMP-4 and 300 ng/mL Flt-3L to the growth factor cocktail did not enhance the detection of hematopoietic clonogenic progenitors from the undifferentiated hES cell lines. Cultures were incubated at 37° C. with 5% $CO_2$ in a humidified atmosphere, and monitored for development of colonies for up to 40 days. Colony subtypes were distinguished by their morphological characteristics, and (in the case of the erythroid lineage) a reddish color denoting hemoglobinization. Results are shown in Table 1.

TABLE 1

CFU Potential of Undifferentiated hES Cells

| hES Cell Line | Wells positive for CFU | | No. of CFU | CFU Subtypes |
|---|---|---|---|---|
| H9 (n = 3) | 1/6 = | 16.6% | 3 | erythroid |
| H1 (n = 4) | 0/9 = | 0% | 0 | (none) |

Undifferentiated hES cells of the H1 line failed to produce hematopoietic colonies in 4 separate experiments, 9 separate wells. Similar results were obtained for undifferentiated H9 cells, with the exception of one experiment in which 3 small erythroid colonies formed.

Example 3

Characterization of MHC Expression on Undifferentiated hES Cells

The expression of MHC antigens on human tissues determines the outcome of allo-specific T cell responses in vitro and in vivo. MHC Class II is expressed primarily on bone marrow derived cells and thymic epithelium. It presents antigen to the immune system for the purpose of initiating a specific immune response. In contrast, MHC Class I is expressed by virtually all mammalian cells. It plays a role in the effector arm of the immune system, and is recognized by specific T lymphocytes when the host cell is virally infected, histo-incompatible, or otherwise contains a foreign antigen.

MHC expression on undifferentiated hES cells was analyzed by immunostaining and flow cytometry. The hES cell lines used in these studies were: H1 (passages 36 to 45), H7 (passages 37 to 43), and H9 (passages 31 to 40). The following antibodies were used: HLA-A, B, C; HLA-DP, DQ, DR (BD-Pharmingen). Cells were incubated with antibody at 0° C., washed, and counterstained with propidium iodide. Flow cytometric analysis was performed on a FACScan™ or FACalibur™ flow cytometer (Becton Dickinson).

FIG. 2 shows the results. Grey line indicates MHC antibody staining; the solid line indicates isotype control. The H1, H7, and H9 hES cell lines all express MHC Class I (n=26), as do human fetal cord blood mononuclear cells (CBMC; n=4). The hES cells have no detectable MHC Class II (DP, DQ, DR haplotypes), whereas a proportion of the CBMCs express a low level of Class II (second hump). The inset in the final panel shows that treatment of the hES cells with 50-100 units of interferon γ (IFN) still failed to induce detectable expression of MHC Class II.

Example 4

Undifferentiated hES Cells are not Immunogenic

The ability of hES cells to induce proliferation of allogeneic T cells was measured in a mixed lymphocyte reaction (MLR). It was found that hES cell lines are unable to induce allo-reactivity in primary human T cells, even after stimulation with IFN-γ.

Peripheral blood mononuclear cells (PBMC) were isolated from heparinized blood using a Ficoll-Hypaque™ density gradient (Amersham Pharmacia), and resuspended in RPMI 1640 medium containing 10% FBS. Alternatively, to enrich for T lymphocytes, separated cells were incubated for 2 h at 37° C., and the non-adherent cells were collected and frozen in 60% AIM-V, 30% fetal bovine serum (FBS), 10% DMSO for later use. Dendritic cells (DCs) were prepared by culturing the remaining adherent cells for 7 d in AIM-V containing 10 ng/ml human recombinant GM-CSF and 10 ng/ml IL-4 (R & D Systems). The mixed lymphocyte reaction was performed as follows: stimulator cells were irradiated (DCs, 3000 Rad; BJ fibroblasts, 3000 Rad; or hES-cell lines, 1000 Rad), and then $1 \times 10^5$ to $1 \times 10^2$ cells were plated in 96-well round bottom plates in AIM-V medium. Responder PBMC or T cells were added at a concentration of $1 \times 10^5$ per well, and the plates were cultured in AIM-V for 5 days. The wells were then pulsed with [$^3$H]thymidine (1 μCi per well) for 16-20 h, harvested, and counted.

FIG. 3 shows the results (mean stimulation index±SEM of multiple wells from 3 donors). hES cells failed to induce allogeneic T cell proliferation in PBMC responders, while significant T cell proliferation was observed when PBMCs were used as stimulators. Similarly, using fetal blood monocytes as responders, no significant proliferation was seen when hES cells were used as stimulators (Panel A). The lack of T cell stimulating capacity of the hES cell lines H1, H7, and H9 was also seen when T cell enriched (monocyte depleted) PBMCs were used as responders (Panel B). Incubation with IFN-γ caused significant up regulation of MHC class I expression (Inset: gray line=untreated hES cells; dotted line=IFN-γ treated cells; dark line=isotype control). However, hES cell lines H1 and H9 prepared by culturing with IFN-γ to increase MHC expression still failed to stimulate T cell proliferation (Panel C). In related experiments, preparing human foreskin fibroblasts by culturing with IFN-γ made them better able to stimulate T cells.

Example 5

Embryoid Body Cells are not Immunogenic

Embryoid bodies were formed from hES cells as follows: confluent cultures of hES cells were treated with collagenase IV and scraped off their Matrigel® attachments in strips. They then were transferred to 6-well low-attachment plates to allow for EB formation by overnight incubation in differentiation medium consisting of knockout D-MEM supplemented with 20% non-heat-inactivated fetal bovine serum, 1% nonessential amino acids, 1 mM L-glutamine, and 0.1 mM β-mercaptoethanol. The EBs were dissociated after 3 or 20 days using 0.4 U/mL collagenase B for 2 h in a 37° C. incubator, followed by treatment with cell dissociation buffer (Invitrogen) for 10 min in a 37° C. water bath. They were then dissociated by gentle pipetting and passage through a 70 μm cell strainer.

EB cells were then tested for their ability to stimulate allogeneic responder lymphocytes in a mixed lymphocyte reaction, as in Example 4.

FIG. 4 (Bottom Panel) shows that human peripheral blood responder lymphocytes were stimulated to proliferate (measured by [$^3$H]Thymidine uptake) by allogeneic stimulator lymphocytes, but not autologous stimulator lymphocytes. hES cells were even less effective stimulators than the autologous lymphocytes, even though they were allogeneic to the responder cells. Embryoid body cells ("differentiated hESC") were equally ineffective stimulators, indicating that they retained the property of the undifferentiated hES cells to inhibit allostimulation.

The Top Panel shows the phenotype of undifferentiated hES cells and their EB progeny. Staining of undifferentiated hES cells for alkaline phosphatase (WO 99/20741) decreased as the cells differentiate to form embryoid bodies. The undifferentiated pPS cell marker SSEA-4 was suppressed in the EB cells, but characteristic B lymphocyte markers CD40, B7.1, and B7.2 did not emerge (the B-lymphoblastoid cell line LG2 is a positive control). The results imply that the ability of the EB cells to inhibit allostimulation was due to a property that progenitor cells in the EBs retained from the hES cells—not to a newly acquired property by differentiation into the hematopoietic cell lineage.

Example 6

Lack of Allostimulation by hES Cells is Due to Active Immunosuppression

An inhibition experiment was performed to determine if the hES cells possess an ability to actively modulate the allo-MHC response to third-party stimulator cells. Responder T cells (1×10$^5$) were cultured for 0 or 2 h with varying numbers of irradiated human fibroblasts and hES cells. Subsequently, 1×10$^4$ irradiated dendritic cells were added per well. After 5 days culture, the cells were pulsed for 16-20 h with [$^3$H]thymidine, washed, and counted.

FIG. 5 shows the results (mean±SEM). The irradiated hES cells abrogated T cell proliferation stimulated by allogeneic dendritic cells. A vigorous proliferative response was detected when PBMCs were co-cultured with allogeneic professional antigen presenting dendritic cells at a ratio of 10:1. However, addition of any of the undifferentiated hES cell lines to these co-cultures strongly inhibited T cell proliferation in vitro (Panel A). Addition of an equivalent number of human fibroblast had no inhibitory effect (Panel A). Serial reduction in the number of hES cells resulted in a gradual loss of the inhibitory effect, showing that inhibition by hES cells of alloactivation in a mixed lymphocyte reaction is dose-dependent (Panel B). The MLR was inhibited at a hES cell:T cell ratio of 1:1 or 1:3.

Example 7

Characterization of the Immunosuppressive Effect of hES Cells

To characterize the inhibitory effect of hES cells, conditioned media was harvested from hES cell cultures and Day 20 cultures of differentiated human embryoid bodies. Supernatants from the cultures was added at 1:2, 1:10, and 1:100 dilutions to allogeneic induced T cell proliferation reactions.

FIG. 6 shows the results. In contrast to inhibitory effect of hES cells, addition of supernatants containing secreted factors had no effect on allogeneic induced T-cell proliferation (Left Panel). The data suggest that inhibitory properties of hES cells were independent of secreted factors and may be mediated by direct membrane interaction.

This possibility was exampled directly by pretreating the hES cells with paraformaldehyde to fix cell membrane cultured with alloreactive T-cells. Fixed hES cells had inhibitory properties that wee similar to untreated hES cells (Right Panel). hES cells apparently have unique immuno-inhibitory properties that are mediated by direct cell membrane interaction, and independent of secreted factors.

The ability of third party hESCs to inhibit alloantigen induced T-cell proliferation suggests that hES cells may be toleragenic. To address this issue, T-cells from primary MLR (1° MLR) reactions were harvested and rechallenged in secondary MLR (2° MLR) reactions.

FIG. 7 shows the results. Similar to previous experiments and autologous control MLR reactions, fixed or non-fixed hES cells did not induce T-cell proliferation compared with allogeneic responding T-cells. As determined by 7-AAD dye exclusion and trypan blue staining, greater than 95% of T-cells harvested from all primary MLR reactions were viable (Left Panel), indicating the absence of T-cell proliferation was not due to cell death induced by co-cultured hESCs.

Upon secondary rechallenge, active responder T-cells derived from primary allo-MLRs continued to proliferate in the presence of alloantigen, or PMA+Imomycin that induces T-cell proliferation via receptor independent mechanisms. However, primary T cell allo-responders failed to proliferate when exposed to hESCs in 2° MLRs, which suggests that hES cells fail to induce T cell alloresponse (Right Panel). Similar effects were observed using T-cell responders from auto-1° MLRs. The T-cells that failed to respond to fixed or non-fixed hES cells in 1° MLRs were still able to proliferate in response to secondary allogeneic stimulation or PMA+Imomycin treatment. In contrast, re-exposure of these 1° MLR responders to human ES cells had no effect on T-cell proliferation.

Without intending to be limited by theory, it is hypothesized that T-cells exposed to hES cells are inhibited from reacting by direct contact with hES cells.

Example 8

Lack of Reaction by the Host Against Undifferentiated hES Cells In Vivo

Transfer of mammalian cells across allogeneic or xenogeneic barriers is met with an immediate inflammatory response easily visualized by leukocyte infiltration to the site of delivery. To assess the immune response to hES cells in vivo, intramuscular injection of undifferentiated hES cells was compared to the human megakaryocytic cell line, MBA-1 (Sirard et al., Blood 83:1575, 1994) and primary fetal blood mononuclear cells in mice.

To validate this assay, hES cells stably transduced with the transgene for green fluorescent protein (WO 01/51616) were harvested and dissociated into single cells suspensions and injected into the quadriceps muscle of recipient mice. The results are shown in FIG. 8 (Top Row). After 24 and 48 hours, injected GFP positive hES cells could be visualized by florescence microscopy in muscle sections, indicating the persistence of implanted hES cells in the murine hosts.

Immune deficient Prk-/-SCID mice were injected intramuscularly with 2 to 5×10$^6$ irradiated hES cells, fetal mononuclear cells, or the MBA-1 human megakaryocyte line. After 48-72 h, tissue was fixed, embedded, and sectioned on a cryostat. Every second section was kept for hematoxylin and eosin (H & E) staining. The presence of leukocytes was identified by their characteristic morphology in H & E-stained sections at 1000× magnification (analysis done blinded; R>0.97).

The Middle Row of FIG. 8 shows the results of this experiment. Both the MBA-1 cells and the mononuclear cord cells were able to induce a granulocytic infiltration response in the Prk−/− SCID mice. In contrast, no granulocyte infiltration was observed at the injection sites of animals injected with irradiated hES cells.

The Bottom Row of FIG. 8 shows the results of a subsequent experiment using wild type immune competent CD-1 mice. Unlike in the Prk-/-SCID mice, injection of endotoxin containing PBS vehicle induced lymphocyte and granulocyte infiltration at the injection site (bottom left panel). However, injection of vehicle together with hES cells completely abrogated leukocyte infiltration (bottom right panel). Injection of MBA-1 cells resuspended in the same vehicle failed to inhibit leukocyte infiltration.

There are two conclusions from this study. First, the hES cells failed to elicit a response against themselves in either immunodeficient or immunocompetent mice. This suggests that they have the capacity to inhibit what should otherwise be a xenogeneic response. Administering cells to a xenogeneic host is in principle a more rigorous test than administering them to an allogeneic human, because of the much higher level of antigen mismatch. Second, the hES cells apparently were also able to inhibit the non-specific infiltration that otherwise occurs in response to endotoxin—an inflammatory response that is not antigen-specific.

As indicated elsewhere in this disclosure, the ability of undifferentiated hES cells to actively inhibit both immune and inflammatory reactions has important implications for clinical therapy.

The skilled reader will appreciate that aspects of this disclosure can be modified as a matter of routine optimization, without departing from the claimed invention

The invention claimed is:

1. A method of inducing a reduced lymphocyte proliferative response to a MHC type presented on an hES cell in a subject, comprising administering to the subject a cell population comprising inactivated undifferentiated hES cells or inactivated embryoid body cells obtained therefrom, thereby obtaining a reduced lymphocyte proliferative response to said MHC type presented on said hES cells than if said cell population had not been administered.

2. The method of claim 1, wherein the cell population has been inactivated by irradiation, treatment with mitomycin c, or fixation with paraformaldehyde.

3. A method of reducing leukocyte infiltration in situ, comprising administering at or around the site of inflammation, a cell population comprising inactivated undifferentiated hES cells or inactivated embryoid body cells obtained therefrom.

4. The method of claim 3, comprising administering at or around the site of inflammation, inactivated undifferentiated hES cells.

5. The method of claim 3, comprising administering at or around the site of inflammation, inactivated embryoid body cells.

6. The method of claim 3, wherein the cell population has been inactivated by irradiation, treatment with mitomycin c, or fixation with paraformaldehyde.

7. A method for inducing a reduced lymphocyte proliferative response to a MHC type presented on an hES cell in a subject, comprising:
   a) administering to the subject a first cell population comprising inactivated undifferentiated hES cells or inactivated embryoid body cells obtained therefrom; and
   b) administering to the subject a second cell population differentiated from the same line of hES cells;
   wherein the subject has a reduced lymphocyte proliferative response to said second cell population compared to a subject that has only been administered the cell population of b.

8. The method of claim 7, wherein the first cell population comprises inactivated undifferentiated hES cells.

9. The method of claim 7, wherein the first cell population comprises inactivated embryoid body cells.

10. The method of claim 7, wherein the first cell population has been inactivated by irradiation, treatment with mitomycin c, or fixation with paraformaldehyde.

11. The method of claim 7, wherein the second cell population is a population of hepatocytes, neurons, oligodendrocytes, cardiomyocytes, osteogenic cells, mesenchymal cells, hematopoietic cells, islet cells, or chondrocytes.

* * * * *